US008304581B2

United States Patent
Uang et al.

(10) Patent No.: US 8,304,581 B2
(45) Date of Patent: Nov. 6, 2012

(54) METHOD OF ENANTIOSELECTIVE ADDITION TO ENONES

(75) Inventors: Biing-Jiun Uang, Hsinchu (TW); Chih-Hao Tseng, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 218 days.

(21) Appl. No.: 12/838,970

(22) Filed: Jul. 19, 2010

(65) Prior Publication Data

US 2011/0282101 A1    Nov. 17, 2011

(30) Foreign Application Priority Data

May 14, 2010   (TW) .............................. 99115442 A

(51) Int. Cl.
*C07C 45/62*   (2006.01)
(52) U.S. Cl. ......... 568/312; 568/355; 568/360; 568/398
(58) Field of Classification Search .................. 568/312, 568/356, 360, 398
See application file for complete search history.

(56) References Cited

OTHER PUBLICATIONS de Vries et al. Enantioselective conjugate addition of diethylzinc to chalcone catalyzed by Co(acac)2 and chiral amino alcohols. Tetrahedron: Asymmetry, Vo. 8 (9), 1997, pp. 1377-1378.*
Wakimoto et al. Catalytic enantioselective conjugate addition of diethylzinc to chalcones using chiral amino alcohol-nickel complexes. Tetrahedron, vol. 58, 2002, pp. 8095-8097.*
Tong et al. Synthesis of N,N-dimethyl-2-amino-1,2-dicyclohexylethanol and its application in the enantioselective conjugate addition of diethylzinc to enones: a convenient upgrade of the chiral ligand via hydrogenation. Tetrahedron: Asymmetry, vol. 12, 2001, pp. 2301-2304.*

* cited by examiner

*Primary Examiner* — Sikarl Witherspoon
(74) *Attorney, Agent, or Firm* — Muncy, Geissler, Olds & Lowe, PLLC

(57) ABSTRACT

The present invention relates to a method of enantioselective addition to enones, including: reacting $R_3(CH_2)_pCH=CR_5C(=O)Y(CH_2)_qR_4$ with $R_6ZnR_7$ in the presence of a compound represented by the following formula (I) and a transition metal catalyst,

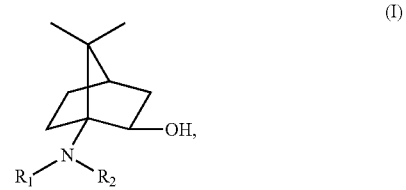

(I)

in which Y, p, q, $R_1$, $R_2$, $R_3$, $R_4$, $R_5$, $R_6$ and $R_7$ are defined the same as the specification. Accordingly, the present invention can perform asymmetric conjugate addition in high yields and enantioselectivity.

19 Claims, No Drawings

METHOD OF ENANTIOSELECTIVE ADDITION TO ENONES

BACKGROUND OF THE INVENTION

1. Field of the Invention

The present invention relates to a method of enantioselective addition to enones and, more particularly, to a method of enantioselective addition of organozinc to enones using a chiral β-amino alcohol.

2. Description of Related Art

Most of isolated natural products have specific stereochemistry. Various stereoconfiguration causes significant difference in bioactivity, and particularly stereoconfiguration is critical for most drugs. For example, thalidomide is a chiral molecule and used for treating sickness and faintness of pregnant women, but its enantiomer causes abnormal fetal development; S,S-isomer of captopril is effective for treating of hypertension and heart disease; and S-isomer of Dopa can be used for treatment of Parkinson's disease, but its R-isomer has toxicity. The U.S. Food and Drug Administration, in 1992, issued that optical isomers of the drug having chiral center(s) should be isolated from each other, studied separately for their bioactivity and taken for clinical testing and only its therapeutically active isomer can be brought to market. Accordingly, many scientists have devoted themselves to the improvement of enantioselectivity to obtain substances having specific stereoconfiguration. The enantioselectivity of products may be enhanced by using chiral reagents, chiral auxiliaries or chiral catalysts, such that products can be synthesized in high optical activity.

Michael addition, also called 1,4-addition or conjugate addition, is one of commonly used methods for forming a C—C bond and widely used in synthesis of natural products and drugs. For example, as shown in Scheme 1, the ketone group on the product from asymmetric 1,4-addition may be modified and transferred into an alcohol or carboxyl group, and bioactive drugs may be obtained through a series of reactions, such as LG121071 (an non-steroidal androgen antagonist), anthracenone (a drug for the treatment of psoriasis), chiral γ-aryl-1H-1,2,4-triazole derivative (an antifungal agent).

Scheme 1. Synthesis of bioactive drugs from optically active adducts

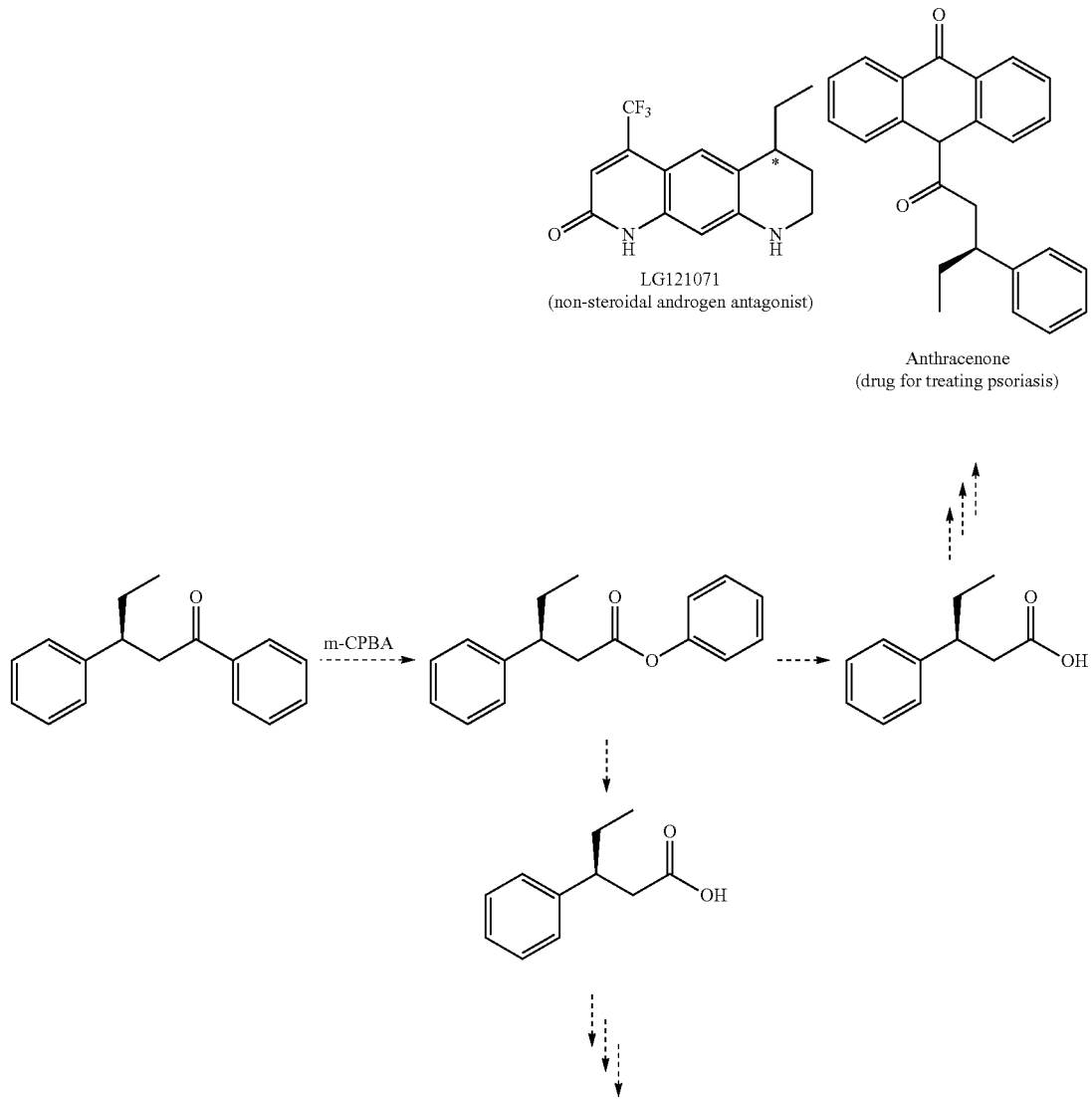

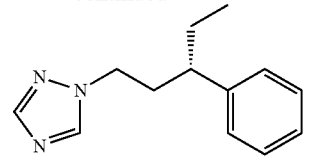

chiral γ-aryl-1H-1,2,4-triazole derivatives
(antifungal agent)

Accordingly, it is an important object of the present invention to develop a highly enantioselective conjugate addition.

SUMMARY OF THE INVENTION

The object of the present invention is to provide a method of enantioselective addition to enones so as to synthesize the conjugate adduct in high optical purity.

To achieve the object, the present invention provides a method of enantioselective addition to enones, including: reacting $R_3(CH_2)_pCH=CR_5C(=O)Y(CH_2)_qR_4$ with $R_6ZnR_7$ in the presence of a compound represented by the following formula (I) and a transition metal catalyst,

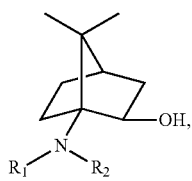

wherein each of $R_1$ and $R_2$ independently is alkyl, or $R_1$ and $R_2$ taken together is $(CH_2)_mX(CH_2)_n$; each of $R_3$ and $R_4$, independently, is alkyl, alkenyl, cycloalkyl, cycloalkenyl, heterocycloalkyl, heterocycloalkenyl, aryl, or heteroaryl, or $R_3$ and $R_4$ taken together is alkylene, alkenylene, cycloalkylene, cycloalkenylene, heterocycloalkylene, heterocycloalkenylene, arylene, or heteroarylene; $R_5$ is hydrogen, halogen, nitro, alkyl, alkenyl, cycloalkyl, cycloalkenyl, heterocycloalkyl, heterocycloalkenyl, aryl, or heteroaryl; each of $R_6$ and $R_7$, independently, is alkyl, alkenyl, cycloalkyl, cycloalkenyl, heterocycloalkyl, heterocycloalkenyl, aryl; X is O, S, or $CH_2$; Y is O, S, or a bond; each of p and q, independently, is an integer of 0 to 30; and each of m and n, independently, is 1, 2 or 3, and the sum of m and n is 3 or 4.

In detail, during the above-mentioned reaction, the compound represented by the formula (I) can be an auxiliary for enantioselective conjugate addition of organozincs (i.e. $R_6ZnR_7$) to enones (i.e. $R_3(CH_2)_pCH=CR_5C(=O)Y(CH_2)_q R_4$). That is, the compound represented by the formula (I) can enhance enantioselectivity of conjugate addition. According to the specific stereoconfiguration of the compound represented by the formula (I) and conformation and steric hindrance of substitutes on the enone, one of the following formulas (II-1) and (II-2) may be prepared in the majority as the conjugate adduct:

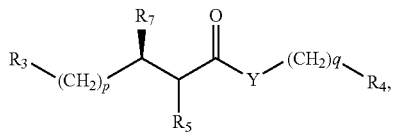

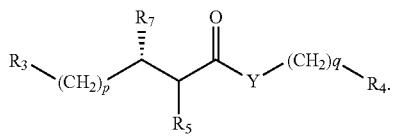

In the present invention, the term "alkyl" refers to a straight or branched hydrocarbon. Examples of alkyl include, but are not limited to, methyl, ethyl, n-propyl, i-propyl, n-butyl, i-butyl, and t-butyl.

In the present invention, the term "alkylene" refers to a straight or branched divalent hydrocarbon. Examples of alkylene include, but are not limited to, methylene ($—CH_2$), ethylene ($—CH_2CH_2—$), and i-propylene ($—CHCH_3CH_2—$).

In the present invention, the term "alkenyl" refers to a straight or branched hydrocarbon containing one or more double bonds. Examples of alkenyl include, but are not limited to, ethenyl, propenyl, allyl, and 1,4-butadienyl.

In the present invention, the term "alkenylene" refers to a straight or branched divalent hydrocarbon containing one or more double bonds. Examples of alkenylene include, but are not limited to, vinylene, and propenylene.

In the present invention, the term "cycloalkyl" refers to a saturated hydrocarbon ring system. Examples of cycloalkyl include, but are not limited to, cyclopropyl, cyclobutyl, cyclopentyl, cycloheptyl, and cyclooctyl.

In the present invention, the term "cycloalkylene" refers to a saturated divalent hydrocarbon ring system. Examples of cycloalkylene include, but are not limited to, cyclopropylene, cyclobutylene, cyclopentylene, cycloheptylene, and cyclooctylene.

In the present invention, the term "cycloalkenyl" refers to a non-aromatic hydrocarbon ring system having one or more double bonds. Examples of cycloalkenyl include, but are not limited to, cyclopentenyl, cyclohexenyl, and cycloheptenyl.

In the present invention, the term "cycloalkenylene" refers to a non-aromatic divalent hydrocarbon ring system having one or more double bonds. Examples of cycloalkenylene include, but are not limited to, cyclopentenylene, cyclohexenylene, and cycloheptenylene.

In the present invention, the term "heterocycloalkyl" refers to a saturated hydrocarbon ring system having one or more ring heteroatoms (e.g., N, O, S or Se). Examples of heterocycloalkyl include, but are not limited to, 4-tetrahydropyranyl.

In the present invention, the term "heterocycloalkylene" refers to a saturated divalent hydrocarbon ring system having one or more ring heteroatoms (e.g., N, O, S or Se).

In the present invention, the term "heterocycloalkenyl" refers to a non-aromatic hydrocarbon ring system having one or more ring heteroatoms (e.g., N, O, S or Se) and one or more ring double bonds. Examples of heterocycloalkenyl include, but are not limited to, pyranyl.

In the present invention, the term "heterocycloalkenylene" refers to a non-aromatic divalent hydrocarbon ring system having one or more ring heteroatoms (e.g., N, O, S or Se) and one or more ring double bonds.

In the present invention, the term "aryl" refers to an aromatic ring system, which may be a 6-carbon monocyclic, 10-carbon bicyclic, 14-carbon tricyclic aromatic ring system. Examples of aryl groups include, but are not limited to, phenyl, naphthyl, and anthracenyl.

In the present invention, the term "arylene" refers to a divalent aromatic ring system, which may be a 6-carbon monocyclic, 10-carbon bicyclic, 14-carbon tricyclic divalent aromatic ring system.

In the present invention, the term "heteroaryl" refers to aromatic ring system having one or more heteroatoms (such as O, N, S, or Se), which may be a 5-8 membered monocyclic, 8-12 membered bicyclic, or 11-14 membered tricyclic aromatic ring system having one or more heteroatoms. Examples of heteroaryl groups include, but are not limited to, pyridyl, furyl, imidazolyl, benzimidazolyl, pyrimidinyl, thienyl, quinolinyl, indolyl, and thiazolyl.

In the present invention, the term "heteroarylene" refers to a divalent aromatic ring system having one or more heteroatoms (such as O, N, S, or Se), which may be a 5-8 membered monocyclic, 8-12 membered bicyclic, or 11-14 membered tricyclic divalent aromatic ring system having one or more heteroatoms.

The above-mentioned alkyl, alkenyl, cycloalkyl, cycloalkenyl, heterocycloalkyl, heterocycloalkenyl, aryl, heteroaryl, alkylene, alkenylene, cycloalkylene, cycloalkenylene, heterocycloalkylene, heterocycloalkenylene, arylene and heteroarylene include both substituted and unsubstituted moieties. The term "substituted" refers to one or more substituents (which may be the same or different), each replacing a hydrogen atom. Examples of substituents include, but are not limited to, halogen (such as F, Cl, Br or I), hydroxyl, amino, alkylamino, arylamino, dialkylamino, diarylamino, cyano, nitro, mercapto, carbonyl, carbamido, carbamyl, carboxyl, thiocyanato, sulfoamido, alkyl, alkenyl, alkoxy, haloalkyl (i.e. alkyl substituted by one or more halogen atoms), aryl, heteroaryl, cyclyl, heterocyclyl, $CO_2$-alkyl and $CO_2$-alkenyl. Among these above-mentioned substituents, alkyl, alkenyl, alkoxy, aryl, heteroaryl, cyclyl, and heterocyclyl may be optionally further substituted with, for example, alkyl, alkenyl, alkoxy, haloalkyl, aryl, heteroaryl, halogen, hydroxyl, amino, mercapto, cyano, nitro, $CO_2$-alkyl or $CO_2$-alkenyl.

Regarding $R_3(CH_2)_pCH=CR_5C(=O)Y(CH_2)_qR_4$, preferably, each of $R_3$ and $R_4$, independently, is unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_iR_a$; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_rCH=CH(CH_2)_kR_a$; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or $R_3$ and $R_4$ taken together is unsubstituted or substituted $C_{1-30}$ alkylene by one or more selected from the group consisting of halogen, cyano, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{2-30}$ alkenylene by one or more selected from the group consisting of halogen, cyano, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ arylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroarylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $R_5$ is hydrogen, halogen, nitro, unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $R_a$ is substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; i is an integer of 1 to 30; and each of r and k independently is an integer of 0 to 30.

Regarding $R_3(CH_2)_pCH$=$CR_5C$(=$O$)$Y(CH_2)_qR_4$, more preferably, each of $R_3$ and $R_4$, independently, is unsubstituted or substituted $C_{1-10}$ alkyl by one or more selected from the group consisting of $C_{6-14}$ aryl and 5-14 membered heteroaryl; $(CH_2)_rR_a$; unsubstituted or substituted $C_{2-10}$ alkenyl by one or more selected from the group consisting of $C_{6-14}$ aryl and 5-14 membered heteroaryl; $(CH_2)_rCH$=$CH(CH_2)_kR_a$; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or $R_3$ and $R_4$ taken together is unsubstituted or substituted $C_{1-10}$ alkylene by one or more selected from the group consisting of halogen, cyano, $C_{1-10}$ alkoxy, $C_{1-10}$ haloalkyl, $CO_2$—$C_{1-10}$ alkyl and $CO_2$—$C_{2-10}$ alkenyl; unsubstituted or substituted $C_{2-10}$ alkenylene by one or more selected from the group consisting of halogen, cyano, $C_{1-10}$ alkoxy, $C_{1-10}$ haloalkyl, $CO_2$—$C_{1-10}$ alkyl and $CO_2$—$C_{2-10}$ alkenyl; unsubstituted or substituted $C_{5-14}$ cycloalkylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted $C_{5-14}$ cycloalkenylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heterocycloalkylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heterocycloalkenylene by one or more selected from the group consisting of halogen, cyano, $C_{1-30}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted $C_{6-14}$ arylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or unsubstituted or substituted 5-14 membered heteroarylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; $R_5$ is hydrogen, halogen, nitro, unsubstituted $C_{1-10}$ alkyl, or unsubstituted $C_{2-10}$ alkenyl; $R_a$ is substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; i is an integer of 1 to 10; and each of r and k independently is an integer of 0 to 10.

Regarding $R_3(CH_2)_pCH$=$CR_5C$(=$O$)$Y(CH_2)_qR_4$, most preferably, $R_5$ is hydrogen or nitro; and $R_3$ and $R_4$ taken together is unsubstituted $C_{1-10}$ alkylene; unsubstituted $C_{2-10}$ alkenylene; unsubstituted phenylene or naphthylene, or each of $R_3$ and $R_4$, independently, is unsubstituted $C_{1-10}$ alkyl (e.g. $(CH_2)_{0-9}CH_3$); substituted $C_{1-10}$ alkyl by phenyl or naphthyl (e.g. $CH_2CH_2C_6H_5$ or $CH_2CH_2C_{10}H_7$); unsubstituted $C_{2-10}$ alkenyl (e.g. $(CH_2)_{0-7}CH$=$CH$); substituted $C_{2-10}$ alkenyl by phenyl or naphthyl (e.g. $CH$=$CHC_6H_5$ or $CH$=$CHC_{10}H_7$); unsubstituted $C_{5-10}$ cycloalkyl (e.g. cyclohexyl); unsubstituted $C_{5-10}$ cycloalkenyl; unsubstituted phenyl or naphthyl; substituted phenyl or naphthyl by one or more selected from the group consisting of halogen, cyano, $C_{1-10}$ alkyl (e.g. $(CH_2)_{0-9}CH_3$), $C_{2-10}$ alkenyl (e.g. $(CH_2)_{0-7}CH$=$CH_2$), $C_{1-10}$ alkoxy (e.g. $O(CH_2)_{0-9}CH_3$), $C_{1-10}$ haloalkyl (e.g. $(CH_2)_{0-9}CF_3$, $(CH_2)_{0-9}CCl_3$, $(CH_2)_{0-9}CBr_3$), $CO_2$—$C_{1-10}$ alkyl (e.g. $CO_2(CH_2)_{0-9}CH_3$) and $CO_2$—$C_{2-10}$ alkenyl (e.g. $CO_2(CH_2)_{0-7}CH$=$CH_2$), in which a substitute on phenyl is preferably at meta- or para-position; $(CH_2)_iR_a$; or $(CH_2)_rCH$=$CH(CH_2)_k R_a$, in which $R_a$ is substituted phenyl or naphthyl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; i is an integer of 1 to 10; and each of r and k independently is an integer of 0 to 8, and the sum of r and k is 8 (e.g. $CH_2CH_2C_6H_4CH_3$, $CH_2CH_2C_{10}H_6CH_3$, $CH$=$CHC_6H_4CH_3$ or $CH$=$CHC_{10}H_6CH_3$).

Examples of $R_3(CH_2)_pCH$=$CR_5C$(=$O$)$Y(CH_2)_qR_4$ include, but are not limited to,

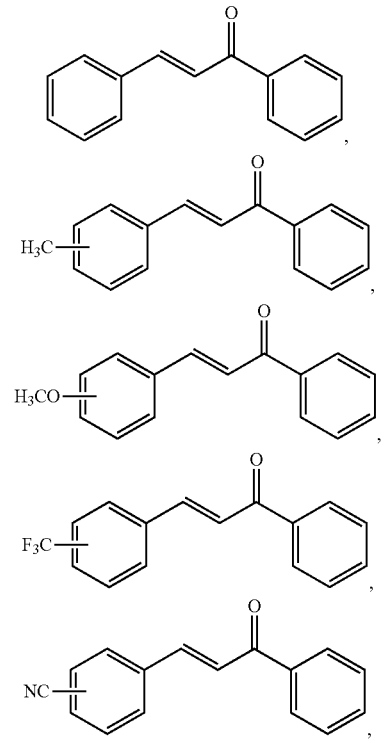

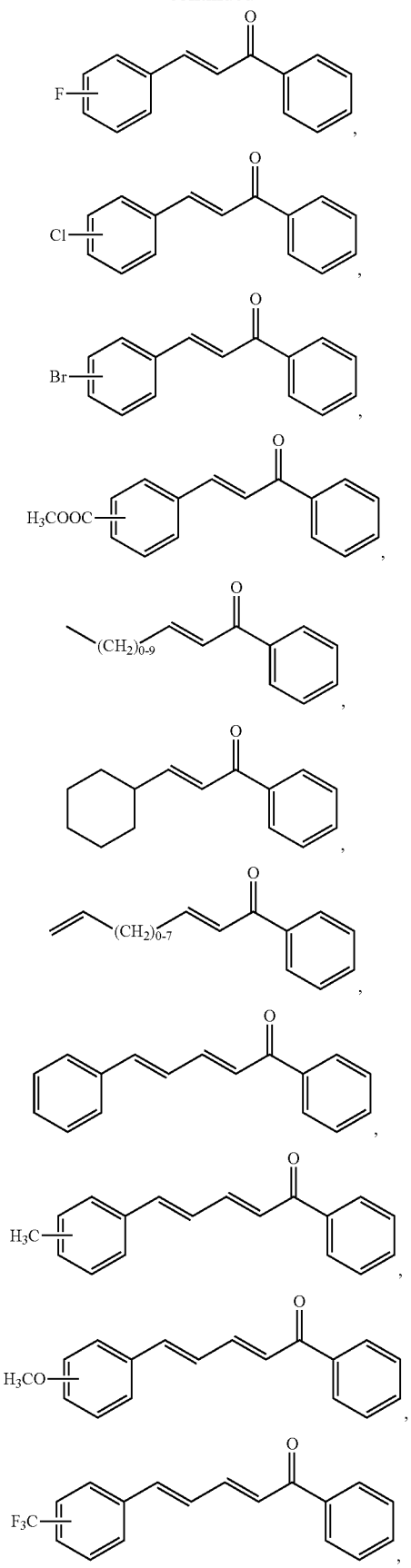

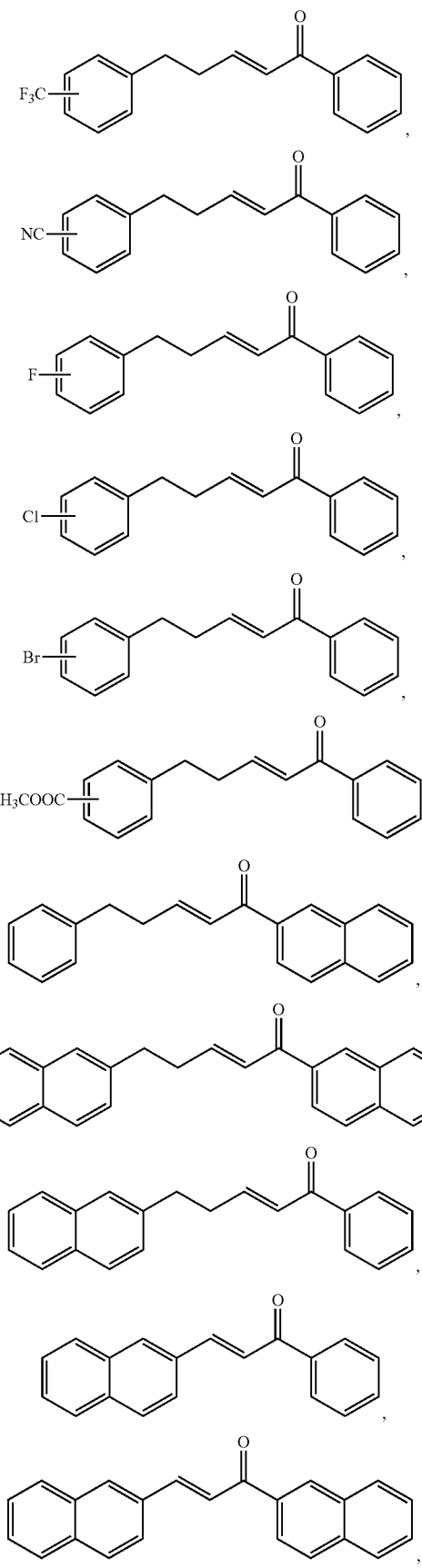
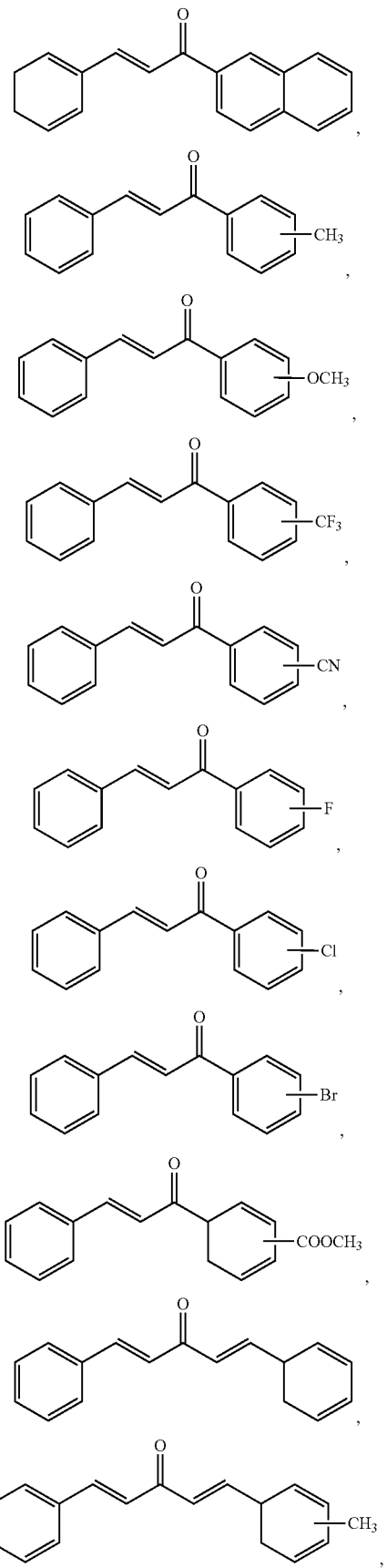

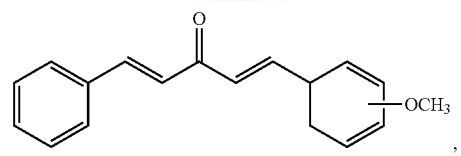
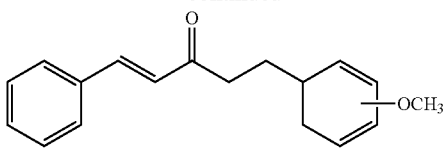
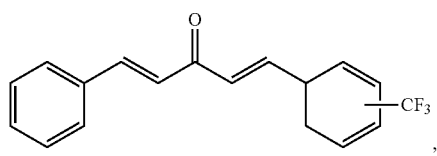
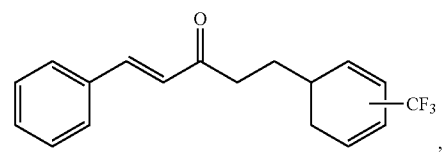
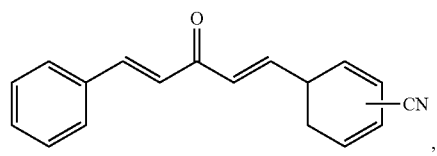
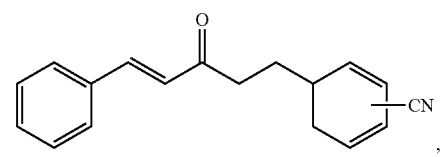
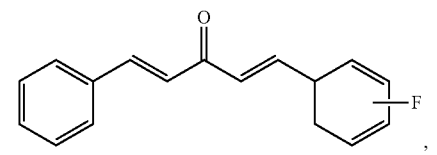
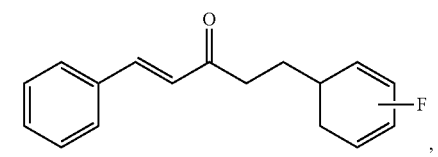
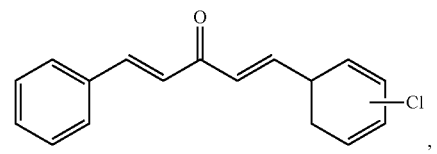
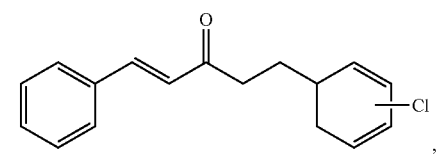
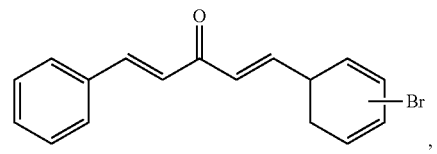
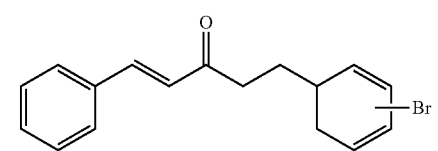
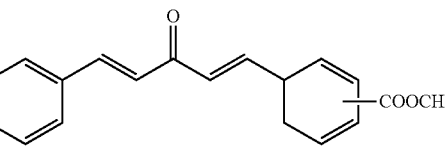
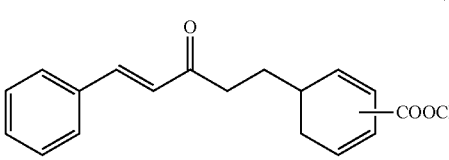
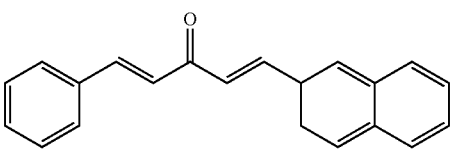
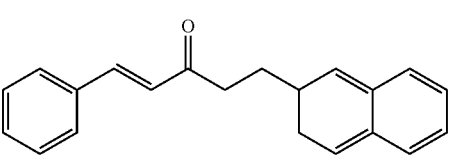
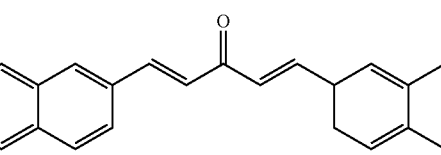
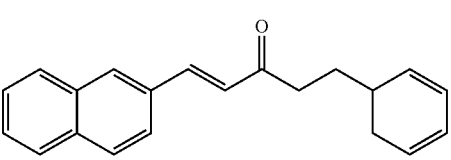
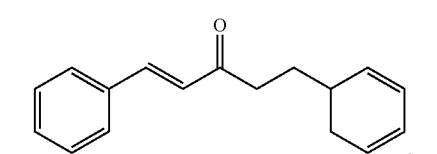
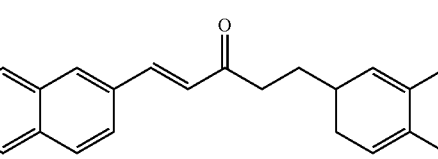
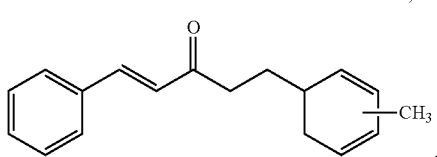
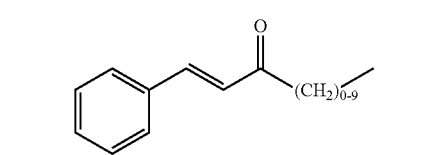

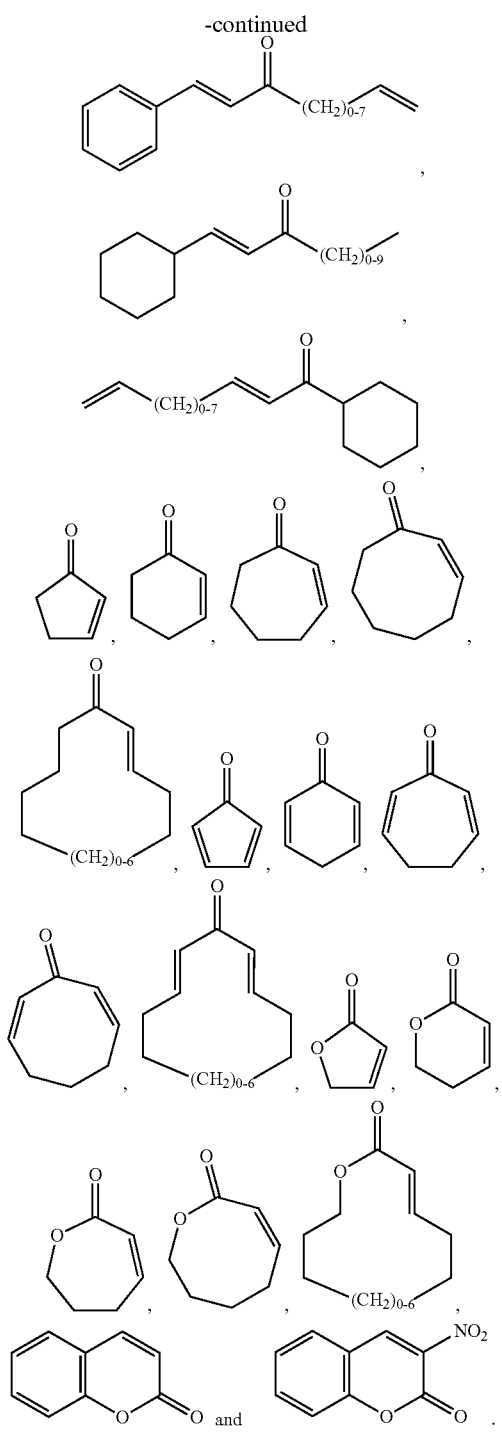

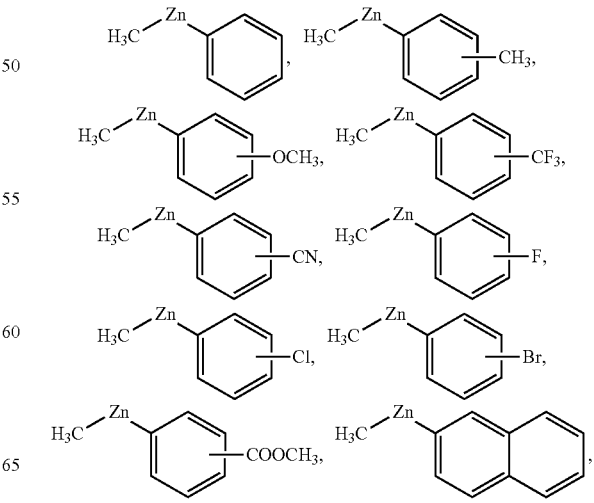

Regarding $R_6ZnR_7$, preferably, each of $R_6$ and $R_7$ independently is unsubstituted or substituted $C_{1-30}$ alkyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; unsubstituted or substituted $C_{2-30}$ alkenyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and $C_{5-14}$ heteroaryl; unsubstituted or substituted $C_{5-14}$ cycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl.

Regarding $R_6ZnR_7$, more preferably, $R_6$ is unsubstituted $C_{1-10}$ alkyl; and $R_7$ is unsubstituted or substituted $C_{1-10}$ alkyl by one or more selected from the group consisting of $C_{6-14}$ aryl and 5-14 membered heteroaryl; unsubstituted or substituted $C_{2-10}$ alkenyl by one or more selected from the group consisting of $C_{6-14}$ aryl and 5-14 membered heteroaryl; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-20}$ alkenyl;

Regarding $R_6ZnR_7$, most preferably, $R_6$ is unsubstituted $C_{1-10}$ alkyl (e.g. $(CH_2)_{0-9}CH_3$); and $R_7$ is unsubstituted $C_{1-10}$ alkyl (e.g. $(CH_2)_{0-9}CH_3$); unsubstituted $C_{2-10}$ alkenyl (e.g. $C(C_2H_5)=CH(C_2H_5)$, $CH=CHC(CH_3)_3$, $CH=CH(CH_2)_{0-7}CH_3$); substituted $C_{2-10}$ alkenyl by phenyl or naphthyl (e.g. $CH=CH(CH_2)_{0-8}C_6H_5$, $CH=CH(CH_2)_{0-8}C_{10}H_7$); unsubstituted phenyl or naphthyl; or substituted phenyl or naphthyl by one or more selected from the group consisting of halogen, cyano, $C_{1-10}$ alkyl (e.g. $(CH_2)_{0-9}CH_3$), $C_{2-10}$ alkenyl (e.g. $(CH_2)_{0-8}CH=CH_2$), $C_{1-10}$ alkoxy (e.g. $O(CH_2)_{0-9}CH_3$), $C_{1-10}$ haloalkyl (e.g. $(CH_2)_{0-9}CF_3$, $(CH_2)_{0-9}CCl_3$, $(CH_2)_{0-9}CBr_3$), $CO_2$—$C_{1-10}$ alkyl (e.g. $CO_2(CH_2)_{0-9}CH_3$) and $CO_2$—$C_{2-10}$ alkenyl (e.g. $CO_2(CH_2)_{0-8}CH=CH_2$).

Examples of $R_6ZnR_7$ include, but are not limited to, $Zn(CH_3)_2$, $Zn(C_2H_5)_2$,

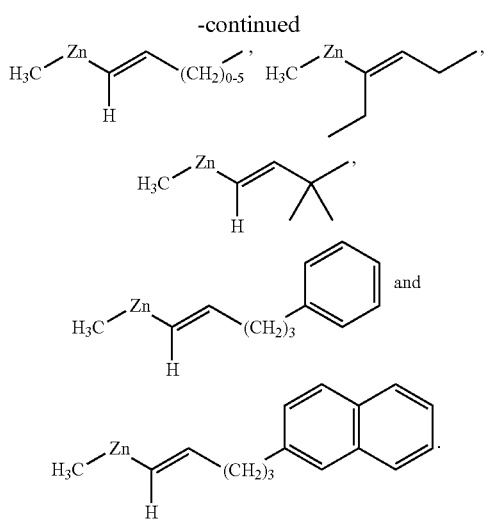

Regarding the compound represented by the formula (I), preferably, the sum of m and n is 4 when X is O or S.

Regarding the compound represented by the formula (I), preferably, m is 1 or 2 and n is 2.

Regarding the compound represented by the formula (I), preferably, X is O or $CH_2$.

Regarding the compound represented by the formula (I), preferably, each of $R_1$ and $R_2$ independently is $C_{1-30}$ alkyl, or $R_1$ and $R_2$ taken together is $(CH_2)_mX(CH_2)_n$; more preferably, each of $R_1$ and $R_2$ independently is $C_{1-10}$ alkyl, or $R_1$ and $R_2$ taken together is $(CH_2)_mX(CH_2)_n$; and most preferably, each of $R_1$ and $R_2$ independently is $C_{1-10}$ alkyl, or $R_1$ and $R_2$ taken together is $(CH_2)_4$, $(CH_2)_5$ or $(CH_2)_2O(CH_2)_2$.

In the method of enantioselective addition according to the present invention, the transition metal catalyst may be any conventional transition metal catalyst commonly used in Michael addition, and preferably is nickel complex, such as $Ni(acac)_2$.

In the method of enantioselective addition according to the present invention, the mole ratio of the compound represented by the formula (I) to the transition metal catalyst may range from 1:1 to 100:1, preferably from 13:1 to 25:1, and more preferably from 13:1 to 15:1.

In the method of enantioselective addition according to the present invention, the compound represented by the formula (I) may be used in an amount of 5 to 20 mol % based on $R_3(CH_2)_pCH=CR_5C(=O)Y(CH_2)_qR_4$.

In the method of enantioselective addition according to the present invention, the transition metal catalyst may be used in an amount from 0.1 to 10 mol %, and preferably from 0.1 to 7 mol % based on $R_3(CH_2)_pCH=CR_5C(=O)Y(CH_2)_qR_4$.

In the method of enantioselective addition according to the present invention, $R_6ZnR_7$ may be used in an amount from 1 to 5 equivalents, preferably from 1 to 3 equivalents, more preferably from 1.2 to 2.5 equivalents, and most preferably from 1.2 to 1.5 equivalents based on $R_3(CH_2)_pCH=CR_5C(=O)Y(CH_2)_qR_4$.

In the method of enantioselective addition according to the present invention, $R_3(CH_2)_pCH=CR_5C(=O)Y(CH_2)_qR_4$ may be reacted with $R_6ZnR_7$ at a temperature in a range from 0° C. to −60° C., preferably from −20° C. to −60° C., and more preferably from −30° C. to −50° C.

In the method of enantioselective addition according to the present invention, $R_3(CH_2)_pCH=CR_5C(=O)Y(CH_2)_qR_4$ may be reacted with $R_6ZnR_7$ in a solvent, and preferably in an aprotic solvent. Herein, the aprotic solvent may be selected from the group consisting of acetonitrile, propionitrile, butyronitrile, isobutyronitrile, tetrahydrofuran, ether, toluene, dichloromethane, n-haxane and a mixture thereof, and preferably is selected from the group consisting of acetonitrile, propionitrile, butyronitrile, isobutyronitrile and a mixture thereof.

In the method of enantioselective addition according to the present invention, the concentration of $R_3(CH_2)_pCH=CR_5C(=O)Y(CH_2)_qR_4$ in the aprotic solvent may range from 0.05 M to 2 M, preferably from 0.1 M to 1 M, more preferably from 0.2 M to 1 M, and most preferably from 0.2 M to 0.5 M.

Accordingly, the present invention uses the above-mentioned compound represented by the formula (I) to perform enantioselective addition of organozincs to enones, so as to prepare ketone adducts in high yield and enantiomeric excess (ee).

Other objects, advantages, and novel features of the invention will become more apparent from the following detailed description when taken in conjunction with the accompanying drawings.

BRIEF DESCRIPTION OF THE DRAWINGS

None.

DETAILED DESCRIPTION OF THE PREFERRED EMBODIMENT

Preparation Example 1

Synthesis of β-Amino Alcohols 5, 6 and 7

Scheme 1. Synthesis of β-amino alcohols 5, 6 and 7

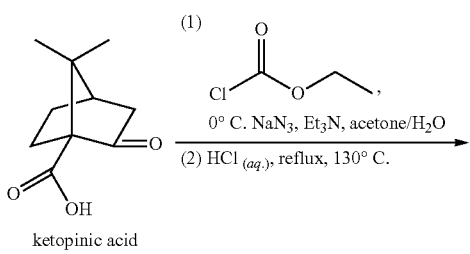

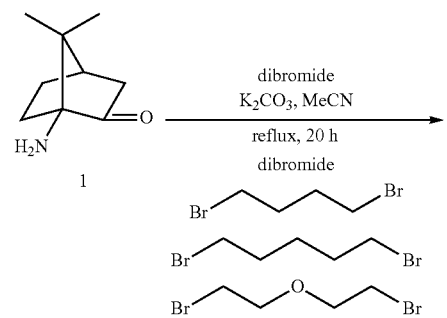

-continued

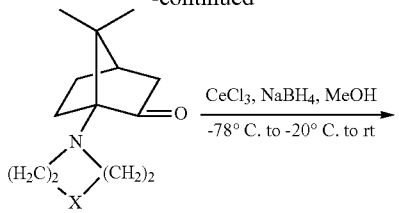

2 X = a bond (85%)
3 X = CH₂ (83%)
4 X = O (88%)

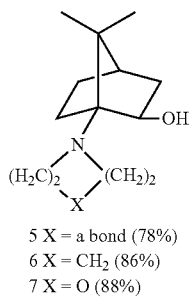

5 X = a bond (78%)
6 X = CH₂ (86%)
7 X = O (88%)

The β-amino alcohol ligands 5-7 were synthesized from ketopinic acid in three steps (Scheme 1). Ketopinic acid was reacted with ethyl chloroformate to form amine ketone 1. Subsequently, treatment of amine ketone 1 with 1,4-butane dibromide, 1,5-pentane dibromide, and bis-(2-bromoethyl) ether gave amino ketones 2-4, respectively. Finally, the diastereoselective reduction of amino ketones 2-4 with NaBH₄/CeCl₃ yielded the corresponding exo-alcohols 5-7, respectively.

1.1. Experimental Procedure for the Synthesis of Amino Ketone 1

To a round-bottomed flask containing ketopinic acid (4.8 g, 26.3 mmol) were added acetone (50 mL) and triethylamine (4 mL), followed by stirring at 0° C. Ethyl chloroformate (5 mL, 52.3 mmol) was gradually dropped thereinto and stirred for 20 minutes. Sodium azide (2.5 g, 38.5 mmol) was dissolved in minimum water and added into the flask, followed by stirring for 1 hour under ice-bath condition. Subsequently, the mixture was warmed to room temperature and stirred for 14 hours. After the reaction was accomplished, the mixture was concentrated to remove acetone, and $HCl_{(aq)}$ (1 N) was added into the flask to adjust the pH value to about 7. The mixture was then extracted with ether, and the combined organic solution was dried over $Na_2SO_4$, filtered and concentrated under high vacuum to give the white solid. The resulting solid was disposed in a flask and $HCl_{(aq)}$ (1 N, 50 mL) was added thereto to perform reaction under reflux for 12 hours. After the reaction was accomplished, the flask was cooled to 0° C., and the pH value was adjusted to about 13 with $NaOH_{(aq)}$ (2N). The mixture was then extracted with ethyl acetate, and the combined organic solution was dried over $Na_2SO_4$, filtered and concentrated under high vacuum to obtain the chiral amino ketone 1 (2.58 g, 64%).

1.2 Experimental Procedure for the Synthesis of Amino Ketones 2-4

Amino ketone 1 (100 mg, 0.65 mmol) and potassium carbonate (200 mg, 1.45 mmol) were added to a 10 mL round-bottomed flask and then the flask was subjected to vacuum conditions. Subsequently, acetonitrile (2.5 mL) and the corresponding dibromide (0.98 mmol) were added thereto in sequence, followed by stirring for 10 minutes. The mixture was heated under reflux for 20 h and then extracted with $CH_2Cl_2$ (5 mL×3). The combined organic solution was dried over $Na_2SO_4$ and concentrated to give the crude product, which was purified via column chromatography (ethyl acetate:n-hexane=1:3) to yield the desired amino ketone 2-4.

《1.2.1. (1S)-7,7-Dimethyl-1-pyrrolidin-1-yl-bicyclo[2.2.1]heptan-2-one 2》

$[α]_D^{24}$=+45.2 (c 1.0, CHCl₃); ¹H NMR (400 MHz, CDCl₃) δ 3.08-3.03 (m, 2H), 2.85-2.81 (m, 2H), 2.41-2.34 (m, 1H), 2.13 (dt, J=12.8, 3.2 Hz, 1H), 2.05-1.98 (m, 1H), 1.91 (t, J=4.6 Hz, 1H), 1.86-1.67 (m, 6H), 1.40-1.33 (m, 1H), 1.08 (s, 3H), 1.06 (s, 3H); ¹³C NMR (100 MHz, CDCl₃) δ 217.4 (C), 77.0 (C), 48.0 (CH₂), 46.9 (C), 42.8 (CH), 42.6 (CH₂), 27.7 (CH₂), 25.9 (CH₂), 24.1 (CH₂), 22.0 (CH₃), 19.7 (CH₃); IR (neat) 2963 (s), 2876 (m), 1742 (s) cm⁻¹; HRMS calcd for C₁₃H₂₁NO 207.1623. found 207.1620.

《1.2.2. (1S)-7,7-Dimethyl-1-piperidin-1-yl-bicyclo[2.2.1]heptan-2-one 3》

$[α]_D^{24}$=+91.4 (c 1.0, CHCl₃); mp 78.0-79.0° C.; ¹H NMR (400 MHz, CDCl₃) δ2.90-2.82 (m, 2H), 2.78-2.70 (m, 2H), 2.42-2.32 (m, 1H), 2.15 (dt, J=12.6, 3.6 Hz, 1H), 2.00-1.90 (m, 1H), 1.88-1.78 (m, 2H), 1.58-1.46 (m, 5H), 1.45-1.39 (m, 2H), 1.36-1.28 (m, 1H), 1.11 (s, 6H); ¹³C NMR (100 MHz, CDCl₃) δ 217.5 (C), 79.2 (C), 49.0 (CH₂), 47.4 (C), 43.6 (CH), 43.0 (CH₂), 26.8 (CH₂), 26.3 (CH₂), 25.7 (CH₂), 24.5 (CH₂), 23.3 (CH₃), 21.1 (CH₃); IR (neat) 2971 (w), 2926 (m), 1739 (s) cm⁻¹; HRMS calcd for C₁₄H₂₃NO 221.1780. found 221.1792.

《1.2.3. (1S)-7,7-Dimethyl-1-morpholin-4-yl-bicyclo[2.2.1]-heptan-2-one 4》

$[α]_D^{24}$=+82.5 (c 1.0, CHCl₃); mp 89.5-90.5° C.; ¹H NMR (400 MHz, CDCl₃) δ 3.63 (t, J=4.8 Hz, 4H), 3.00-2.90 (m, 2H), 2.81-2.76 (m, 2H), 2.39-2.33 (m, 1H), 2.08 (dt, J=12.4, 3.6 Hz, 1H), 2.00-1.92 (m, 1H), 1.85-1.80 (m, 2H), 1.57-1.50 (m, 1H), 1.34-1.31 (m, 1H), 1.09 (s, 3H), 1.08 (s, 3H); ¹³C NMR (100 MHz, CDCl₃) δ 217.1 (C), 78.6 (C), 67.7 (CH₂), 48.5 (CH₂), 47.5 (C), 43.8 (CH), 43.1 (CH₂), 26.0 (CH₂), 25.8 (CH₂), 23.3 (CH₃), 21.0 (CH₃); IR (neat) 2958 (s), 2889 (m), 2850 (s), 1743 (s) cm⁻¹; HRMS calcd for C₁₃H₂₁NO₂ 223.1572. found 223.1567.

1.3. Experimental Procedure for the Synthesis of β-Amino Alcohols 5-7

A 25 mL round-bottomed flask containing the chiral amino ketone 2-4 (0.45 mmol), CeCl₃ (0.28 g, 0.11 mmol), and methanol (3 mL) was cooled to −78° C., followed by the addition of NaBH₄ (0.08 g, 2.11 mmol). The flask was slowly warmed to −20° C. After 2 h at −20° C., the flask was slowly warmed to 25° C., and was kept at ambient temperature for 6 h. The solvents were then removed in vacuo, followed by extraction with CH₂Cl₂ (15 mL×3). The organic solution was dried over Na₂SO₄, filtered and concentrated, to give the crude product, which was purified by column chromatography (ethyl acetate:n-hexane=1:3) to yield the chiral amino alcohol 5-7.

《1.3.1. (1S,2R)-7,7-Dimethyl-1-pyrrolidin-1-yl-bicyclo[2.2.1]-heptan-2-ol 5》

$[α]_D^{24}$=+1.2 (c 1.0, CHCl₃); ¹H NMR (400 MHz, CDCl₃) δ 3.97 (br, 1H), 3.66 (dd, J=7.8, 3.0 Hz, 1H), 2.67-2.62 (m, 2H), 2.55-2.50 (m, 2H), 1.90-1.85 (m, 1H), 1.81-1.60 (m, 7H), 1.51 (t, J=4.4 Hz, 1H), 1.16-1.06 (m, 1H), 1.10 (s, 3H), 1.03-0.96 (m, 1H), 0.99 (s, 3H); $^{13}$C NMR (100 MHz, CDCl$_3$) δ 75.1 (CH), 70.1 (C), 47.0 (CH$_2$), 46.3 (C), 45.7 (CH), 38.4 (CH$_2$), 26.1 (CH$_2$), 22.9 (CH$_2$), 22.8 (CH$_3$), 20.7 (CH$_2$), 20.1 (CH$_3$); IR (neat) 3422 (br), 2958 (s), 2877 (s), 2821 (m) cm$^{-1}$; HRMS calcd for C$_{13}$H$_{23}$NO 209.1780. found 209.1774.

《1.3.2. (1S,2R)-7,7-Dimethyl-1-piperidin-1-yl-bicyclo[2.2.1]-heptan-2-ol 6》

$[α]_D^{24}$=+14.2 (c 1.0, CHCl$_3$); mp 88.5-89.5° C.; $^1$H NMR (400 MHz, CDCl$_3$) δ 3.72 (d, J=5.2 Hz, 1H), 2.58 (br, 4H), 1.90-1.70 (m, 3H), 1.68-1.36 (m, 8H), 1.18-0.98 (m, 2H), 1.14 (s, 3H), 1.07 (s, 3H); $^{13}$C NMR (100 MHz, CDCl$_3$) δ 73.6 (CH), 72.8 (C), 48.4 (CH$_2$), 46.7 (CH), 45.9 (C), 37.9 (CH$_2$), 26.7 (CH$_2$), 26.3 (CH$_2$), 24.4 (CH$_2$), 24.0 (CH$_3$), 22.3 (CH$_2$) 20.3 (CH$_3$); IR (neat) 3329 (br), 2958 (s), 2932 (s), 2805 (w) cm$^{-1}$; HRMS calcd for C$_{14}$H$_{25}$NO 223.1936. found 223.1945.

《1.3.3. (1S,2R)-7,7-Dimethyl-1-morpholin-4-yl-bicyclo[2.2.1]heptan-2-ol 7》

$[α]_D^{24}$=+11.0 (c 1.0, CHCl$_3$); mp 35.0-36.0° C.; $^1$H NMR (400 MHz, CDCl$_3$) δ 3.74-3.66 (m, 5H), 2.67-2.61 (m, 2H), 2.57-2.50 (m, 2H), 1.92-1.76 (m, 3H), 1.69-1.62 (m, 1H), 1.52 (t, J=4.6 Hz, 1H), 1.18-1.00 (m, 2H), 1.14 (s, 3H), 1.06 (s, 3H); $^{13}$C NMR (100 MHz, CDCl$_3$) δ 72.8 (CH), 71.8 (C), 66.7 (CH$_2$), 47.2 (CH$_2$), 46.0 (CH), 45.3 (C), 37.5 (CH$_2$), 25.7 (CH$_2$), 23.3 (CH$_3$), 21.7 (CH$_2$), 19.8 (CH$_3$); IR (neat) 3415 (br), 2956 (s), 2884 (s), 2850 (m) cm$^{-1}$; HRMS calcd for C$_{13}$H$_{23}$NO$_2$ 225.1729. found 225.1713; Elemental analysis: calcd: C, 69.29; H, 10.29; N, 6.22. found: C, 69.49; H, 9.39; N, 6.24.

Preparation Example 2

Synthesis of β-Amino Alcohol 9

Scheme 2. Synthesis of β-amino alcohol 9

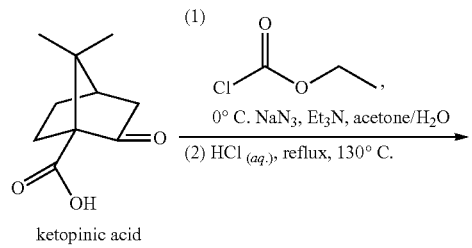

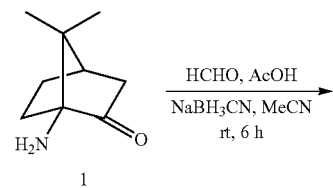

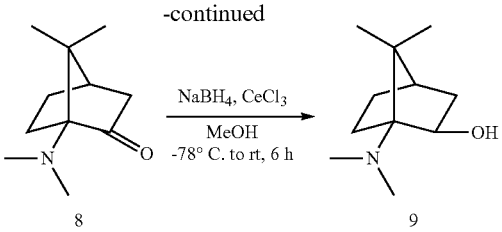

The β-amino alcohol ligand 9 was synthesized from ketopinic acid in three steps (Scheme 2). Ketopinic acid was reacted with ethyl chloroformate to form amine ketone 1. Subsequently, alkylation of amine ketone 1 with formaldehyde, acetic acid and sodium cyanoborohydride gave amino ketone 8. Finally, the diastereoselective reduction of amino ketone 8 with NaBH$_4$/CeCl$_3$ yielded the corresponding exo-alcohol 9.

2.1. Experimental Procedure for the Synthesis of Amino Ketone 1

The chiral amino ketone 1 was prepared by the procedure described in the preparation example 1.

2.2. Experimental Procedure for the Synthesis of Amino Ketone 8

To a 10 mL round-bottomed flask were added amino ketone 1 (0.1 g, 1.30 mmol), formaldehyde (37% solution, 0.3 mL, 4.03 mmol) and acetonitrile (3 mL). After the addition of NaBH$_3$CN (0.17 g, 2.71 mmol) at 0° C., the mixture was warmed to room temperature and stirred for 15 minutes. Acetic acid (0.30 mL) was then gradually dropped thereto and stirred for 6 hours, followed by the addition of NaOH$_{(aq)}$ (2N) to adjust the pH value to a range from 8 to 9. The mixture was extracted with ether (15 mL×3), and the combined organic solution was dried over Na$_2$SO$_4$, filtered and concentrated to give crude product, which was purified by column chromatography (methanol:dichloromethane=1:20) to yield the colorless oil 8 (0.2 g, 86%).

《2.2.1. 1-Dimethylamino-7,7-dimethyl-bicyclo[2.2.1]heptan-2-one 8》

$^1$H NMR (400 MHz, CDCl$_3$) δ 2.51 (s, 6H), 2.43-2.34 (m, 1H), 2.16-2.08 (m, 1H), 2.03-1.94 (m, 1H), 1.90-1.82 (m, 2H), 1.66-1.57 (m, 1H), 1.40-1.32 (m, 1H), 1.13 (s, 3H), 1.12 (s, 3H); $^{13}$C NMR (100 MHz, CDCl$_3$) δ 217.4 (C), 78.5 (C), 47.3 (C), 43.8 (CH), 42.9 (CH$_2$), 41.1 (CH$_3$), 26.8 (CH$_2$), 25.7 (CH$_2$), 23.0 (CH$_3$), 20.7 (CH$_3$); IR (neat) 2954 (s), 2880 (m), 2795 (w), 1744 (s) cm$^{-1}$; HRMS calcd for C$_{11}$H$_{19}$NO 153.1154. found 153.1145.

2.3. Experimental Procedure for the Synthesis of β-Amino Alcohol 9

The procedure for preparing β-amino alcohol 9 was the same as that for preparing β-amino alcohols 5-7 described in the preparation example 1, except that the present preparation example uses amino ketone 8 to replace amino ketones 2-4 used in the preparation example 1.

《2.3.1 1-Dimethylamino-7,7-dimethyl-bicyclo[2.2.1]heptan-2-one 9》

$^1$H NMR (400 MHz, CDCl$_3$) δ 3.71 (dd, J=7.8, 3.0 Hz, 1H), 2.24 (s, 6H), 1.92-1.71 (m, 4H), 1.68-1.58 (m, 2H), 1.54-1.57 (m, 1H), 1.15 (s, 3H), 1.06 (s, 3H); $^{13}$C NMR (100 MHz, CDCl$_3$) δ 74.2 (CH), 72.1 (C), 46.4 (CH), 46.0 (C), 40.2 (CH$_3$), 38.0 (CH$_2$), 26.0 (CH$_2$), 23.7 (CH$_3$), 20.4 (CH$_2$) 20.1

(CH$_3$); IR (neat) 3405 (br), 2954 (s), 2880 (m) cm$^{-1}$; HRMS calcd for C$_{11}$H$_{21}$NO 155.1310. found 155.1294.

Reaction Example 1

Michael Addition by β-Amino Alcohols 5-7 and 9

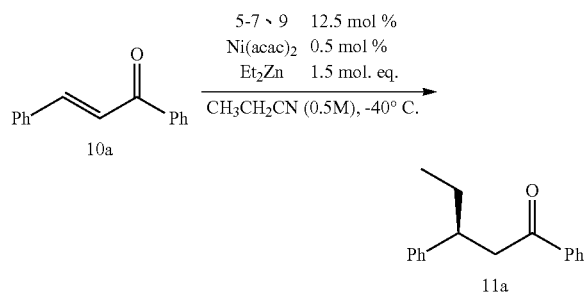

TABLE 1

| Entry | Chiral amino alcohol | Time (h) | Yield$^a$ (%) | ee$^b$ (%) |
| --- | --- | --- | --- | --- |
| 1 | 5 | 22 | 82 | 76 |
| 2 | 6 | 17 | 73 | 91 |
| 3 | 7 | 20 | 84 | 90 |
| 4 | 9 | 22 | 71 | 41 |

$^a$Isolated yield after column chromatography.
$^b$Determination by HPLC on the AD-H chiral column.

As shown in Table 1, the highest yield 84% and high enantioselectivity 90% (ee) were obtained in the case of the substitutes on the chiral amino alcohol being a morpholinyl group (entry 3). In the case of replacing the morpholinyl group by a piperidinyl group, high enantioselectivity 91% (ee) and moderate yield were obtained (entry 2). Additionally, as shown in Table 1, when the six membered cyclic substitute was replaced by the five membered cyclic pyrrolidinyl group, enantiomeric excess (ee) was reduced to 76% owing to steric hindrance being reduced (entry 1). Similarly, enantiomeric excess (ee) was reduced to 41% in the case of using a dimethyl amino group as a substitute (entry 4). Thereby, from Table 1, it can be known that higher yield 84% and enantioselectivity 90% (ee) would be obtained when using the chiral amino alcohol 7 in the reaction.

《1.1. Experimental Procedure of Entry 1》

To a flask were added chiral ligand 5 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (1.5 mL, 1.5 mmol, 1.0 M in n-hexane) was gradually dropped thereto via a 250 μL gas tight syringe to perform reaction for 22 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《1.2. Experimental Procedure of Entry 2》

To a flask were added chiral ligand 6 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (1.5 mL, 1.5 mmol, 1.0 M in n-hexane) was gradually dropped thereto via a 250 μL gas tight syringe to perform reaction for 17 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《1.3. Experimental Procedure of Entry 3》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (1.5 mL, 1.5 mmol, 1.0 M in n-hexane) was gradually dropped thereto via a 250 μL gas tight syringe to perform reaction for 20 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《1.4. Experimental Procedure of Entry 4》

To a flask were added chiral ligand 9 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (1.5 mL, 1.5 mmol, 1.0 M in n-hexane) was gradually dropped thereto via a 250 μL gas tight syringe to perform reaction for 22 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

Reaction Example 2

Optimization of the Reaction Conditions with Respect to Enantioselective Addition of Organozinc to Enones Through the following reactions, the effect of various reaction parameters on yield and enantiomeric excess (ee) were examined, and the results were shown in the following tables 2 to 6. Herein, the concentration (M) shown in solvent brackets refers to the concentration of enones in a solvent.

2.1. β-Amino Alcohol 7/Nickel Complex Mole Ratio

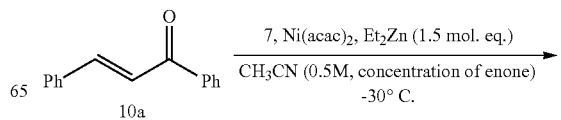

-continued

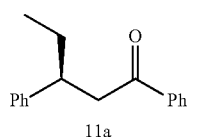

11a

TABLE 2

| Entry | 7 (mol %) | Ni(acac)$_2$ (mol %) | Time (h) | Yield[a] (%) | ee[b] (%) |
|---|---|---|---|---|---|
| 1[c] | 10 | — | 30 | 6 | 81 |
| 2[d] | — | 7.0 | 20 | 61 | — |
| 3 | 20 | 1.5 | 4 | 82 | 83 |
| 4 | 16 | 7.0 | 1.5 | 84 | 79 |
| 5 | 12.5 | 1.0 | 5.5 | 76 | 77 |
| 6 | 12.5 | 0.5 | 2.5 | 85 | 82 |
| 7 | 10 | 1.0 | 2.0 | 88 | 73 |
| 8 | 10 | 0.5 | 6.5 | 80 | 79 |
| 9 | 10 | 0.1 | 16 | 67 | 80 |
| 10 | 5 | 1.0 | 4.0 | 83 | 53 |

[a]Isolated yield after column chromatography.
[b]Determination by HPLC on the AD-H chiral column.
[c]Addition of no Ni(acac)$_2$.
[d]Addition of no β-amino alcohol 7.

As shown in Table 2, the best enantioselectivity was obtained by using β-amino alcohol 7/nickel complex mole ratio in 20:1.5 (entry 3), and the highest yield and high enantioselectivity were obtained in the case of β-amino alcohol 7/nickel complex mole ratio being 12.5:0.5 (entry 6).

《2.1.1. Experimental Procedure of Entry 1》

To a flask were added chiral ligand 7 (0.10 mmol), acetonitrile (1.0 mL) and enone (1 mmol) dissolved in acetonitrile (1.0 mL), and the mixture was stirred for 15 min at room temperature. After being cooled to −30° C., diethylzinc solution (1.5 mL, 1.5 mmol, 1.0 M in n-hexane) was gradually dropped thereto via a 250 μL gas tight syringe to perform reaction for 30 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.1.2. Experimental Procedure of Entry 2》

To a flask were added Ni(acac)$_2$ (0.07 mmol), acetonitrile (1.0 mL) and enone (1 mmol) dissolved in acetonitrile (1.0 mL), and the mixture was stirred for 15 min at room temperature. After being cooled to −30° C., diethylzinc solution (1.5 mL, 1.5 mmol, 1.0 M in n-hexane) was gradually dropped thereto via a 250 μL gas tight syringe to perform reaction for 20 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.1.3. Experimental Procedure of Entry 3》

To a flask were added chiral ligand 7 (0.20 mmol), Ni(acac)$_2$ (0.015 mmol) and acetonitrile (1.0 mL) to perform reaction under reflux for 1 h. The flask was then cooled to room temperature, followed by the addition of enone (1 mmol) dissolved in acetonitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 4 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.1.4. Experimental Procedure of Entry 4》

To a flask were added chiral ligand 7 (0.16 mmol), Ni(acac)$_2$ (0.07 mmol) and acetonitrile (1.0 mL) to perform reaction under reflux for 1 h. The flask was then cooled to room temperature, followed by the addition of enone (1 mmol) dissolved in acetonitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 1.5 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.1.5. Experimental Procedure of Entry 5》

To a flask were added chiral ligand 7 (0.125 mmol), Ni(acac)$_2$ (0.01 mmol) and acetonitrile (1.0 mL) to perform reaction under reflux for 1 h. The flask was then cooled to room temperature, followed by the addition of enone (1 mmol) dissolved in acetonitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 5.5 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.1.6. Experimental Procedure of Entry 6》

To a flask were added chiral ligand 7 (0.125 mmol), Ni(acac)$_2$ (0.005 mmol) and acetonitrile (1.0 mL) to perform reaction under reflux for 1 h. The flask was then cooled to room temperature, followed by the addition of enone (1 mmol) dissolved in acetonitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 2.5 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.1.7. Experimental Procedure of Entry 7》

To a flask were added chiral ligand 7 (0.10 mmol), Ni(acac)$_2$ (0.01 mmol) and acetonitrile (1.0 mL) to perform reaction under reflux for 1 h. The flask was then cooled to room temperature, followed by the addition of enone (1 mmol) dissolved in acetonitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 2 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.1.8. Experimental Procedure of Entry 8》

To a flask were added chiral ligand 7 (0.10 mmol), Ni(acac)$_2$ (0.005 mmol) and acetonitrile (1.0 mL) to perform reaction under reflux for 1 h. The flask was then cooled to room temperature, followed by the addition of enone (1 mmol) dissolved in acetonitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 6.5 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.1.9. Experimental Procedure of Entry 9》

To a flask were added chiral ligand 7 (0.10 mmol), Ni(acac)$_2$ (0.001 mmol) and acetonitrile (1.0 mL) to perform reaction under reflux for 1 h. The flask was then cooled to room temperature, followed by the addition of enone (1 mmol) dissolved in acetonitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 16 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.1.10. Experimental Procedure of Entry 10》

To a flask were added chiral ligand 7 (0.05 mmol), Ni(acac)$_2$ (0.01 mmol) and acetonitrile (1.0 mL) to perform reaction under reflux for 1 h. The flask was then cooled to room temperature, followed by the addition of enone (1 mmol) dissolved in acetonitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 4 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

2.2. Solvent Effect

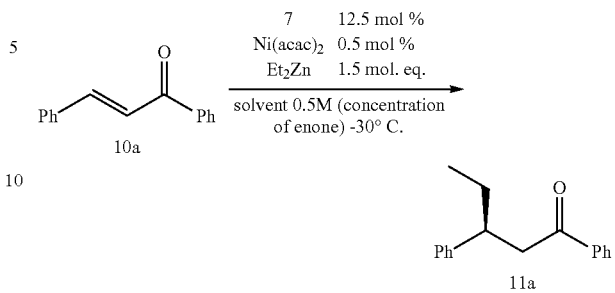

TABLE 3

| Entry | Solvent | Time (h) | Yield$^a$ (%) | ee$^b$ (%) |
|---|---|---|---|---|
| 1 | CH$_3$CN | 2.5 | 85 | 82 |
| 2 | CH$_3$CH$_2$CN | 6.0 | 86 | 86 |
| 3 | CH$_3$CH$_2$CH$_2$CN | 6.0 | 81 | 87 |
| 4 | (CH$_3$)$_2$CHCN | 21 | 77 | 85 |
| 5 | THF | 5.5 | 88 | 63 |
| 6 | ether | 5.5 | 68 | 47 |
| 7 | toluene | 4.0 | 50 | 55 |
| 8 | CH$_2$Cl$_2$ | 4.0 | 48 | 42 |
| 9 | n-hexane (0.2M) | 17 | 13 | 68 |

$^a$Isolated yield after column chromatography.
$^b$Determination by HPLC on the AD-H chiral column.

As shown in Table 3, adducts were prepared in higher yield and enantioselectivity by using acetonitrile, propionitrile, butyronitrile or isobutyronitrile as a solvent.

《2.2.1. Experimental Procedure of Entry 1》

To a flask were added chiral ligand 7 (0.125 mmol), Ni(acac)$_2$ (0.005 mmol) and acetonitrile (1.0 mL) to perform reaction under reflux for 1 h. The flask was then cooled to room temperature, followed by the addition of enone (1 mmol) dissolved in acetonitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 2.5 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.2.2. Experimental Procedure of Entry 2》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 6 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

⟨2.2.3. Experimental Procedure of Entry 3⟩

To a flask were added chiral ligand 7 (0.125 mmol), Ni(acac)$_2$ (0.005 mmol) and butyronitrile (1.0 mL) to perform reaction under reflux for 1 h. The flask was then cooled to room temperature, followed by the addition of enone (1 mmol) dissolved in butyronitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 6 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

⟨2.2.4. Experimental Procedure of Entry 4⟩

To a flask were added chiral ligand 7 (0.125 mmol), Ni(acac)$_2$ (0.005 mmol) and isobutyronitrile (1.0 mL) to perform reaction under reflux for 1 h. The flask was then cooled to room temperature, followed by the addition of enone (1 mmol) dissolved in isobutyronitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 21 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

⟨2.2.5. Experimental Procedure of Entry 5⟩

To a flask were added chiral ligand 7 (0.125 mmol), Ni(acac)$_2$ (0.005 mmol) and THF (1.0 mL) to perform reaction under reflux for 1 h. The flask was then cooled to room temperature, followed by the addition of enone (1 mmol) dissolved in THF (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 5.5 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

⟨2.2.6. Experimental Procedure of Entry 6⟩

To a flask were added chiral ligand 7 (0.125 mmol), Ni(acac)$_2$ (0.005 mmol) and ether (1.0 mL) to perform reaction under reflux for 1 h. The flask was then cooled to room temperature, followed by the addition of enone (1 mmol) dissolved in ether (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 5.5 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

⟨2.2.7. Experimental Procedure of Entry 7⟩

To a flask were added chiral ligand 7 (0.125 mmol), Ni(acac)$_2$ (0.005 mmol) and toluene (1.0 mL) to perform reaction under reflux for 1 h. The flask was then cooled to room temperature, followed by the addition of enone (1 mmol) dissolved in toluene (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 4 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

⟨2.2.8. Experimental Procedure of Entry 8⟩

To a flask were added chiral ligand 7 (0.125 mmol), Ni(acac)$_2$ (0.005 mmol) and dichloromethane (1.0 mL) to perform reaction under reflux for 1 h. The flask was then cooled to room temperature, followed by the addition of enone (1 mmol) dissolved in dichloromethane (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 4 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

⟨2.2.9. Experimental Procedure of Entry 9⟩

To a flask were added chiral ligand 7 (0.125 mmol), Ni(acac)$_2$ (0.005 mmol) and n-hexane (1.0 mL) to perform reaction under reflux for 1 h. The flask was then cooled to room temperature, followed by the addition of enone (1 mmol) dissolved in n-hexane (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 17 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct 11a.

2.3. Temperature Effect

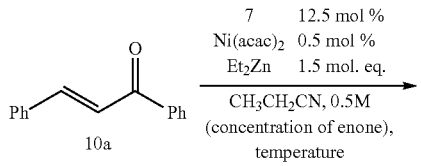

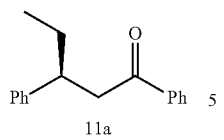
11a

TABLE 4

| Entry | Time (h) | Temperature (° C.) | Yield$^a$ (%) | ee$^b$ (%) |
| --- | --- | --- | --- | --- |
| 1 | 6.0 | −20 | 73 | 84 |
| 2 | 6.0 | −30 | 86 | 86 |
| 3 | 21 | −40 | 87 | 90 |
| 4 | 36 | −50 | 84 | 92 |

$^a$Isolated yield after column chromatography.
$^b$Determination by HPLC on the AD-H chiral column.

As shown in Table 4, enantioselectivity was enhanced to 90% (ee) by reducing the temperature from −30° C. to −40° C., and enantioselectivity can be further enhanced to 92% (ee) when the temperature was reduced to −50° C.

《2.3.1. Experimental Procedure of Entry 1》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −20° C., diethylzinc solution (1.5 mL, 1.5 mmol, 1.0 M in n-hexane) was gradually dropped thereto via a 250 μL gas tight syringe to perform reaction for 6 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.3.2. Experimental Procedure of Entry 2》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −30° C., diethylzinc solution (1.5 mL, 1.5 mmol, 1.0 M in n-hexane) was gradually dropped thereto via a 250 μL gas tight syringe to perform reaction for 6 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.3.3. Experimental Procedure of Entry 3》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (1.5 mL, 1.5 mmol, 1.0 M in n-hexane) was gradually dropped thereto via a 250 μL gas tight syringe to perform reaction for 21 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.3.4. Experimental Procedure of Entry 4》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −50° C., diethylzinc solution (1.5 mL, 1.5 mmol, 1.0 M in n-hexane) was gradually dropped thereto via a 250 μL gas tight syringe to perform reaction for 36 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

2.4. Concentration Effect

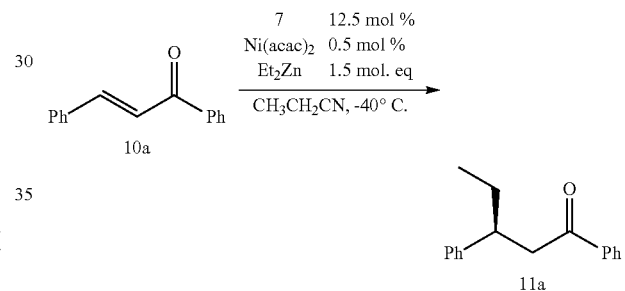

TABLE 5

| Entry | Concentration of 10a (M) | Time (h) | Yield$^a$ (%) | ee$^b$ (%) |
| --- | --- | --- | --- | --- |
| 1 | 1.0 | 20 | 83 | 89 |
| 2 | 0.5 | 21 | 87 | 90 |
| 3 | 0.2 | 25 | 76 | 90 |
| 4$^c$ | 0.5 | 18 | 79 | 88 |

$^a$Isolated yield after column chromatography.
$^b$Determination by HPLC on the AD-H chiral column.
$^c$Addition of diethylzinc in 1.1M of toluene.

As shown in Table 5, enantioselectivity was enhanced to 90% (ee) and yield was 87% in the case of the concentration being 0.5 M, and enantioselectivity 90% (ee) was maintained and yield was decreased to 76% in the case of the concentration being 0.2 M.

《2.4.1. Experimental Procedure of Entry 1》

To a flask were added chiral ligand 7 (0.125 mmol), Ni(acac)$_2$ (0.005 mmol) and propionitrile (0.5 mL) to perform reaction under reflux for 1 h. The flask was then cooled to room temperature, followed by the addition of enone (1 mmol) dissolved in propionitrile (0.5 mL) and stirring for 15 minutes at room temperature. After being cooled to −40° C., diethylzinc solution (1.5 mL, 1.5 mmol, 1.0 M in n-hexane)

was gradually dropped thereto via a 250 μL gas tight syringe to perform reaction for 20 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.4.2. Experimental Procedure of Entry 2》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (1.5 mL, 1.5 mmol, 1.0 M in n-hexane) was gradually dropped thereto via a 250 μL gas tight syringe to perform reaction for 21 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.4.3. Experimental Procedure of Entry 3》

To a flask were added chiral ligand 7 (0.125 mmol), Ni(acac)$_2$ (0.005 mmol) and propionitrile (2.5 mL) to perform reaction under reflux for 1 h. The flask was then cooled to room temperature, followed by the addition of enone (1 mmol) dissolved in propionitrile (2.5 mL) and stirring for 15 minutes at room temperature. After being cooled to −40° C., diethylzinc solution (1.5 mL, 1.5 mmol, 1.0 M in n-hexane) was gradually dropped thereto via a 250 μL gas tight syringe to perform reaction for 25 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.4.4. Experimental Procedure of Entry 4》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (1.36 mL, 1.5 mmol, 1.1 M in toluene) was gradually dropped thereto via a 250 μL gas tight syringe to perform reaction for 18 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

2.5. Amount Effect of Et$_2$Zn

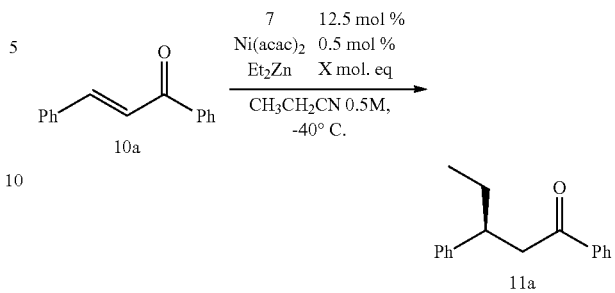

TABLE 6

| Entry | Diethylzinc (equiv.) | Time (h) | Yield$^a$ (%) | ee$^b$ (%) |
|---|---|---|---|---|
| 1 | 1.2 | 21 | 60 | 91 |
| 2 | 1.5 | 21 | 87 | 90 |
| 3 | 2.0 | 21 | 85 | 87 |
| 4 | 2.5 | 21 | 84 | 85 |

$^a$Isolated yield after column chromatography.
$^b$Determination by HPLC on the AD-H chiral column.

As shown in Table 6, enantioselectivity was increased to 91% (ee) and yield was 60% by decreasing the amount of diethylzinc to 1.2 equivalents. However, enantioselectivity was decreased from 90% (ee) to 85% (ee) and excellent yield 84-87% was obtained in the case of increasing the amount of diethylzinc from 1.5 equivalents to 2.5 equivalents.

《2.5.1. Experimental Procedure of Entry 1》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (1.2 mL, 1.2 mmol, 1.0 M in n-hexane) was gradually dropped thereto via a 250 μL gas tight syringe to perform reaction for 21 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.5.2. Experimental Procedure of Entry 2》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (1.5 mL, 1.5 mmol, 1.0 M in n-hexane) was gradually dropped thereto via a 250 μL gas tight syringe to perform reaction for 21 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.5.3. Experimental Procedure of Entry 3》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (2.0 mL, 2.0 mmol, 1.0 M in n-hexane) was gradually dropped thereto via a 250 μL gas tight syringe to perform reaction for 21 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《2.5.4. Experimental Procedure of Entry 4》

To a flask were added chiral ligand 7 (0.125 mmol), Ni(acac)$_2$ (0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −40° C., diethylzinc solution (2.5 mL, 2.5 mmol, 1.0 M in n-hexane) was gradually dropped thereto via a 250 μL gas tight syringe to perform reaction for 21 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

Reaction Example 3

Asymmetric Addition of Organozinc to Various Enones

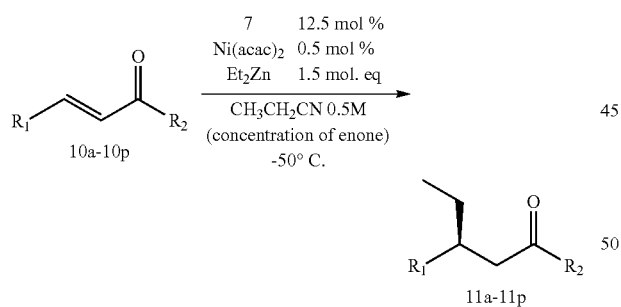

TABLE 7

| Entry | R$_1$ | R$_2$ | | Time (h) | Yield[a] (%) | ee[b] (%) |
|---|---|---|---|---|---|---|
| 1 | Ph | Ph | 10a | 36 | 84 | 92 |
| 2 | p-MeC$_6$H$_4$ | Ph | 10b | 48 | 81 | 89 |
| 3 | p-MeOC$_6$H$_4$ | Ph | 10c | 50 | 82 | 89 |
| 4[c] | p-CF$_3$C$_6$H$_4$ | Ph | 10d | 48 | 76 | 91 |
| 5[c] | p-NCC$_6$H$_4$ | Ph | 10e | 48 | 93 | 87 |
| 6 | p-FC$_6$H$_4$ | Ph | 10f | 30 | 87 | 89 |
| 7 | p-ClC$_6$H$_4$ | Ph | 10g | 48 | 87 | 87 |
| 8[c] | p-BrC$_6$H$_4$ | Ph | 10h | 30 | 76 | 90 |
| 9 | m-ClC$_6$H4 | Ph | 10i | 24 | 83 | 92 |

TABLE 7-continued

| Entry | R$_1$ | R$_2$ | | Time (h) | Yield[a] (%) | ee[b] (%) |
|---|---|---|---|---|---|---|
| 10 | m-MeOC$_6$H$_4$ | Ph | 10j | 48 | 83 | 91 |
| 11 | o-MeOC$_6$H$_4$ | Ph | 10k | 48 | 80 | 51 |
| 12 | o-ClC$_6$H$_4$ | Ph | 10l | 48 | 67 | 81 |
| 13 | Ph | p-MeOC$_6$H$_4$ | 10m | 48 | 67 | 89 |
| 14 | Ph | m-MeOC$_6$H$_4$ | 10n | 48 | 90 | 87 |
| 15[d] | c-C6H11 | Ph | 10o | 48 | 42 | 70 |
| 16[c] | Me | Ph | 10p | 48 | 71 | 64 |

[a]Isolated yield after column chromatography.
[b]Determination by HPLC on the AD-H chiral column.
[c]CH$_3$CH$_2$CN (0.34M).
[d]11o being R form.

As shown in Table 7, high yield and enantioselectivity can be obtained in the case of the substitute on phenyl group being at the meta- or para-position.

3.1. General Procedure for the Asymmetric Addition of Diethylzinc to Enones

To a flask were added chiral ligand 7 (0.028 g, 0.125 mmol), Ni(acac)$_2$ (0.0013 g, 0.005 mmol) and propionitrile (1.0 mL) to perform reaction under reflux for 1 h. The flask was then cooled to room temperature, followed by the addition of enone (1 mmol) dissolved in propionitrile (1.0 mL) and stirring for 15 minutes at room temperature. After being cooled to −50° C., diethylzinc solution (1.5 mL, 1.5 mmol, 1.0 M in n-hexane) was gradually dropped thereto via a 250 μL gas tight syringe to perform reaction for 48 hours. The reaction was stopped by the addition of HCl$_{(aq)}$ (1 N). The mixture was extracted with ether, and the combined organic solution was dried over Na$_2$SO$_4$, filtered and concentrated to give the crude product, which was purified by column chromatography (ethyl acetate:n-hexane=1:9) to yield the corresponding adduct.

《3.1.1. 1,3-Diphenyl-1-pentanone 11a》

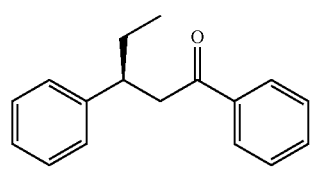

11a $^1$H NMR (400 MHz, CDCl$_3$) δ 7.91-7.89 (m, 2H), 7.54-7.51 (m, 1H), 7.44-7.40 (m, 2H), 7.31-7.16 (m, 5H), 3.31-3.22 (m, 3H), 1.83-1.75 (m, 1H), 1.70-1.61 (m, 1H), 0.81 (t, J=7.2 Hz, 3H); $^{13}$C NMR (100 MHz, CDCl$_3$) δ 199.4 (C), 144.5 (CH), 137.2 (CH), 132.8 (CH), 128.4 (CH), 128.3 (CH), 128.0 (CH), 127.6 (CH), 126.2 (CH), 45.7, (CH$_2$), 43.1 (CH), 29.1 (CH$_2$), 12.2 (CH$_3$); IR (KBr) ν=3062, 3028, 2963, 2930, 2875, 1682, 1597, 1449, 1368, 1279, 1201, 1180, 1104, 1075, 1015, 978, 924 cm$^{-1}$; $[\alpha]_D^{24}$=+7.4 (c 1.0, EtOH).

《3.1.2. 1-Phenyl-3-(4-methylphenyl)pentanone 11b》

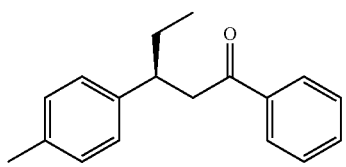

$^1$H NMR (400 MHz, CDCl$_3$) δ 7.92 (d, J=8.0 Hz, 2H), 7.3 (t, J=6.8 Hz, 1H), 7.43 (t, J=7.2 Hz, 2H), 7.10-7.15 (m, 4H), 3.23-3.30 (m, 3H), 2.32 (s, 3H), 1.76-1.82 (m, 1H), 1.61-1.68 (m, 1H), 0.83 (t, J=7.2 Hz, 3H); $^{13}$C NMR (100 MHz, CDCl$_3$) δ 199.2 (C), 141.5 (C), 137.2 (C), 135.5 (C), 132.8 (CH), 129.0 (CH), 128.4 (CH), 128.0 (CH), 127.4 (CH), 45.6 (CH$_2$), 42.5 (CH), 29.1 (CH$_2$), 20.9 (CH$_3$), 12.0 (CH$_3$); IR (KBr) ν=3063, 3023, 2963, 2923, 2875, 1683, 1597, 1581, 1514, 1448, 1361, 1279, 1248, 1199, 1116, 1017, 978, 923, 817 cm$^{-1}$; $[\alpha]_D^{24}$=+14.2 (c 1.0, EtOH).

《3.1.3. 1-Phenyl-3-(4-methoxyphenyl)-pentanone 11c》

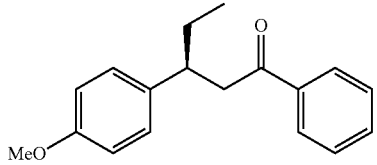

$^1$H NMR (400 MHz, CDCl$_3$) δ 7.88 (d, J=8.0 Hz, 2H), 7.49-7.53 (t, 1H), 7.39-7.43 (t, 2H), 7.11 (d, J=8.8 Hz, 2H), 6.80 (d, J=8.4 Hz, 2H), 3.75 (s, 3H), 3.14-3.24 (m, 3H), 1.69-1.77 (m, 1H), 1.54-1.63 (m, 1H), 0.79 (t, J=7.6 Hz, 3H); $^{13}$C NMR (100 MHz, CDCl$_3$) δ 199.4 (C), 157.9 (C), 137.3 (C), 136.6 (C), 132.8 (CH), 128.5 (CH), 128.5 (CH), 128.0 (CH), 113.7 (CH), 55.2 (CH$_3$), 45.8 (CH$_2$), 42.2 (CH), 29.3 (CH$_2$), 12.1 (CH$_3$); IR (KBr) ν=3060, 3031, 2997, 2960, 2931, 2874, 2835, 1682, 1611, 1597, 1581, 1513, 1448, 1363, 1248, 1178, 1115, 1036, 978, 923, 830 cm$^{-1}$; $[\alpha]_D^{24}$=+16.0 (c 1.0, EtOH).

《3.1.4. 1-Phenyl-3-(4-trifluoromethyl-phenyl)-pentanone 11d》

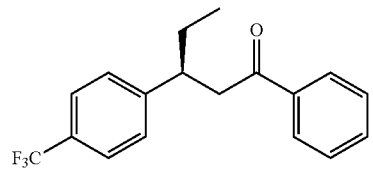

$^1$H NMR (400 MHz, CDCl$_3$) δ 7.90 (d, J=8.0 Hz, 2H), 7.52 (t, J=6.8 Hz, 3H), 7.42 (t, J=7.6 Hz, 2H), 7.35 (d, J=8.0 Hz, 2H), 3.29-3.34 (m, 3H), 1.64-1.69 (m, 1H), 1.78-1.83 (m, 1H), 0.81 (t, J=7.2 Hz, 3H); $^{13}$C NMR (100 MHz, CDCl$_3$) δ 198.3 (C), 148.9 (C), 136.9 (C), 133.0 (CH), 128.8 (CH), 128.5 (CH), 127.9 (CH), 125.2 (CH), 122.9 (C), 44.9 (CH$_2$), 42.6 (CH), 29.0 (CH$_2$), 11.8 (CH$_3$); IR (KBr) ν=3064, 2966, 2933, 2878, 1689, 1618, 1598, 1449, 1391, 1279, 1247, 1164, 1119, 1068, 1017, 980, 923, 840 cm$^{-1}$; $[\alpha]_D^{24}$=−6.8 (c 1.0, EtOH).

《3.1.5. 1-Phenyl-3-(4-cyanophenyl)-pentanone 11e》

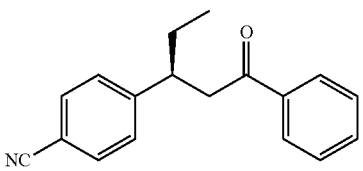

$^1$H NMR (400 MHz, CDCl$_3$) δ 7.77 (d, J=7.2 Hz, 2H), 7.41-7.45 (m, 3H), 7.35 (d, J=7.6 Hz, 2H), 7.23 (d, J=8.2 Hz, 2H), 3.17-3.23 (m, 3H), 1.50-1.57 (m, 1H), 1.66-1.71 (m, 1H), 0.69 (t, J=7.2 Hz, 3H); $^{13}$C NMR (100 MHz, CDCl$_3$) δ 198.0 (C), 150.4 (C), 136.7 (C), 133.0 (CH), 132.0 (CH), 128.5 (CH), 128.4 (CH), 127.8 (CH), 118.8 (C), 109.9 (C), 44.6 (CH$_2$), 42.8 (CH), 28.9 (CH$_2$), 11.8 (CH$_3$); IR (KBr) ν=3064, 2964, 2931, 2876, 2227, 1683, 1607, 1505, 1449, 1214, 1179, 1017, 978, 838 cm$^{-1}$; $[\alpha]_D^{24}$=−17.8 (c 1.0, EtOH).

《3.1.6. 1-Phenyl-3-(4-fluorophenyl)pentanone 11f》

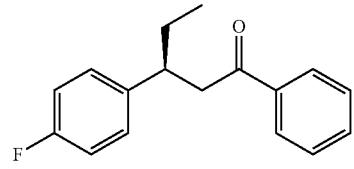

$^1$H NMR (400 MHz, CDCl$_3$) δ 7.87 (d, 2H), 7.49-7.53 (m, 1H), 7.39-7.43 (m, 2H), 7.15-7.20 (m, 2H), 6.95-6.98 (m, 2H), 3.20-3.27 (m, 3H), 1.74-1.81 (m, 1H), 1.57-1.64 (m, 1H), 0.80 (t, J=7.2 Hz, 3H); $^{13}$C NMR (100 MHz, CDCl$_3$) δ 198.9 (C), 161.2 (C), 140.2 (C), 137.0 (C), 132.9 (CH), 128.9 (CH), 128.4 (CH), 127.9 (CH), 115.0 (CH), 45.5 (CH$_2$), 42.2 (CH), 29.3 (CH$_2$), 11.9 (CH$_3$); IR (KBr) ν=3063, 2963, 2931, 2876, 2227, 1683, 1599, 1581, 1510, 1449, 1362, 1278, 1222, 1159, 1109, 1015, 976, 923, 834 cm$^{-1}$; $[\alpha]_D^{24}$=+5.1 (c 1.0, EtOH).

《3.1.7. 1-Phenyl-3-(4-chlorophenyl)pentanone 11g》

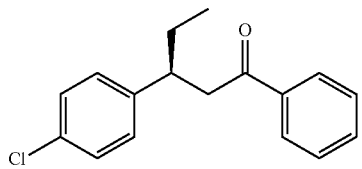

$^1$H NMR (400 MHz, CDCl$_3$) δ7.82-7.88 (m, 2H), 7.50-7.54 (m, 1H), 7.37-7.44 (m, 2H), 7.20-7.24 (m, 2H), 7.11-7.17 (m, 2H), 3.21 (m, 3H), 1.72-1.77 (m, 1H), 1.52-1.61 (m, 1H), 0.77 (t, J=7.2 Hz, 3H); $^{13}$C NMR (100 MHz, CDCl$_3$) δ198.8 (C), 143.1 (C), 137.1 (C), 133.0 (CH), 131.8 (C), 129.0 (CH), 128.6 (CH), 128.5 (CH), 128.0 (CH), 45.4 (CH$_2$), 42.3 (CH), 29.2 (CH$_2$), 12.0 (CH$_3$); IR (KBr) v=3062, 3028, 2963, 2930, 2875, 1684, 1596, 1580, 1491, 1448, 1362, 1275, 1245, 1213, 1180, 1092, 1013, 979, 829 cm$^{-1}$; $[\alpha]_D^{24}$=+1.4 (c 1.0, EtOH).

《3.1.8. 1-Phenyl-3-(4-bromophenyl)pentanone 11h》

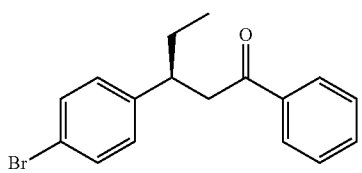

$^1$H NMR (400 MHz, CDCl$_3$) δ 7.88 (d, J=7.2 Hz, 2H), 7.49-7.54 (m, 1H), 7.36-7.43 (m, 4H), 7.10 (d, J=6.8 Hz, 2H), 3.19-3.25 (m, 3H), 1.73-1.80 (m, 1H), 1.56-1.63 (m, 1H), 0.79 (t, J=7.6 Hz, 3H); $^{13}$C NMR (100 MHz, CDCl$_3$) δ 198.5 (C), 143.6 (C), 136.9 (C), 132.9 (CH), 131.3 (CH), 129.3 (CH), 128.5 (CH), 127.9 (CH), 119.8 (C), 45.2 (CH$_2$), 42.2 (CH), 29.1 (CH$_2$), 11.9 (CH$_3$); IR (KBr) v=3061, 3027, 2963, 2931, 2875, 1689, 1597, 1580, 1487, 1449, 1361, 1273, 1244, 1213, 1181, 1073, 1010, 979, 923, 825 cm$^{-1}$; $[\alpha]_D^{24}$=+1.4 (c 1.0, EtOH).

《3.1.9. 1-Phenyl-3-(3-chlorophenyl)pentanone 11i》

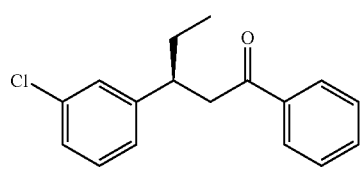

$^1$H NMR (400 MHz, CDCl$_3$) δ7.92 (d, J=7.6 Hz, 2H), 7.54-7.57 (m, 1H), 7.43-7.47 (m, 2H), 7.13-7.27 (m, 4H), 3.27 (m, 3H), 1.71-1.83 (m, 1H), 1.60-1.67 (m, 1H), 0.83 (t, J=6.8 Hz, 3H); $^{13}$C NMR (100 MHz, CDCl$_3$) δ198.6 (C), 146.8 (C), 137.0 (C), 134.1 (C), 133.0 (CH), 129.6 (CH), 128.5 (CH), 128.0 (CH), 127.6 (CH), 126.4 (CH), 126.0 (CH), 45.2 (CH$_2$), 42.6 (CH), 29.1 (CH$_2$), 12.0 (CH$_3$); IR (KBr) v=3062, 2964, 2932, 2875, 1683, 1597, 1574, 1449, 1362, 1202, 1086, 1001, 979, 880 cm$^{-1}$; $[\alpha]_D^{24}$=-4.4 (c 1.0, EtOH).

《3.1.10. 1-Phenyl-3-(3-methoxyphenyl)pentanone 11j》

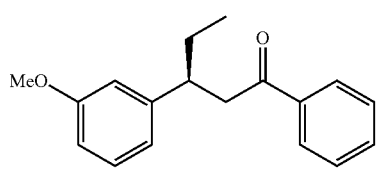

$^1$H NMR (400 MHz, CDCl$_3$) δ7.90 (d, J=7.6 Hz, 2H), 7.50 (m, 1H), 7.40 (m, 2H), 7.20 (t, J=8.0 Hz, 1H), 6.83 (d, J=7.2 Hz, 1H), 6.79 (s, 1H), 6.72 (d, J=8.0 Hz, 1H), 3.77 (s, 3H), 3.20-3.29 (m, 3H), 1.76-1.79 (m, 1H), 1.61-1.67 (m, 1H), 0.82 (t, J=7.2 Hz, 3H); $^{13}$C NMR (100 MHz, CDCl$_3$) δ199.0 (C), 159.5 (C), 146.3 (C), 137.1 (C), 132.8 (CH), 129.2 (CH), 128.4 (CH), 127.9 (CH), 119.9 (CH), 113.5 (CH), 111.1 (CH), 54.9 (CH$_3$), 45.4 (CH$_2$), 42.9 (CH), 29.0 (CH$_2$), 12.0 (CH$_3$); IR (KBr) v=3028, 2961, 2931, 2874, 2836, 1682, 1598, 1583, 1487, 1449, 1362, 1214, 1155, 1045, 979, 874 cm$^{-1}$; $[\alpha]_D^{24}$=+5.9 (c 1.0, EtOH).

《3.1.11. 1-Phenyl-3-(2-methoxyphenyl)pentanone 11k》

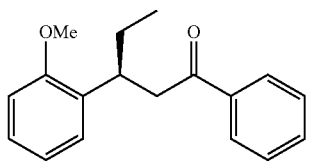

$^1$H NMR (400 MHz, CDCl$_3$) δ 8.00 (d, J=8.0 Hz, 2H), 7.56-7.60 (m, 1H), 7.48 (t, J=7.6 Hz, 2H), 7.21-7.30 (m, 2H), 6.97 (t, J=7.2 Hz, 1H), 6.90 (d, J=8.4 Hz, 1H), 3.88 (s, 3H), 3.69-3.76 (m, 1H), 3.24-3.40 (m, 2H), 1.78-1.86 (m, 2H) 0.88 (t, J=7.2 Hz, 3H); $^{13}$C NMR (100 MHz, CDCl$_3$) δ 199.5 (C), 157.2 (C), 137.1 (C), 132.5 (CH), 132.2 (C), 128.2 (CH), 127.9 (CH), 127.8 (CH), 126.9 (CH), 120.3 (CH), 110.5 (CH), 55.0 (CH$_3$), 44.3 (CH$_2$), 36.8 (CH), 27.1 (CH$_2$), 11.9 (CH$_3$); IR (KBr) v=3063, 3028, 2962, 2934, 2874, 2837,

《3.1.12. 1-Phenyl-3-(2-chlorophenyl)pentanone 11l》

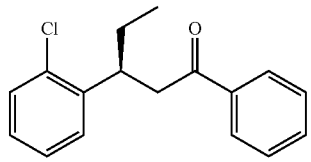

11l $^1$H NMR (400 MHz, CDCl$_3$) δ7.93 (d, J=7.2 Hz, 2H), 7.53 (m, 1H), 7.40-7.50 (m, 2H), 7.34 (d, J=7.6 Hz, 1H), 7.20-7.26 (m, 2H), 7.08-7.18 (m, 1H), 3.83-3.90 (m, 1H), 3.17-3.34 (m, 2H), 1.71-1.83 (m, 1H), 1.64-1.86 (m, 2H), 0.82 (t, J=7.6 Hz, 3H); $^{13}$C NMR (100 MHz, CDCl$_3$) δ 198.6 (C), 141.7 (C), 136.8 (C), 134.2 (C), 132.9 (CH), 129.6 (CH), 128.4 (CH), 128.0 (CH), 127.9 (CH), 127.2 (CH), 126.8 (CH), 44.3 (CH$_2$), 38.5 (CH), 27.9 (CH$_2$), 11.6 (CH$_3$); IR (KBr) v=3064, 2964, 2933, 2874, 1686, 1596, 1474, 1448, 1365, 1202, 1034, 973, 750 cm$^{-1}$; $[\alpha]_D^{24}$=−32.0 (c 1.0, EtOH).

《3.1.13. 1-(4-methoxyphenyl)-3-phenyl-pentanone 11m》

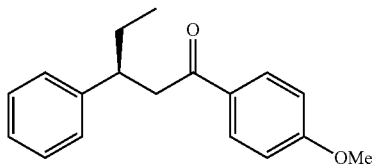

11m $^1$H NMR (400 MHz, CDCl$_3$) δ7.90 (d, J=8.8 Hz, 2H), 7.16-7.30 (m, 5H), 6.91 (d, J=8.8 Hz, 2H), 7.11 (d, J=8.8 Hz, 2H), 3.86 (s, 3H), 3.18-3.25 (m, 3H), 1.76-1.80 (m, 1H), 1.61-1.68 (m, 1H), 0.80 (t, J=7.2 Hz, 3H); $^{13}$C NMR (100 MHz, CDCl$_3$) δ 197.7 (C), 163.3 (C), 144.8 (C), 130.3 (CH), 128.3 (CH), 127.6 (CH), 126.1 (CH), 113.6 (CH), 55.4 (CH$_3$), 45.2 (CH$_2$), 43.1 (CH), 29.1 (CH$_2$), 12.0 (CH$_3$); IR (KBr) v=3030, 2950, 2930, 2875, 1674, 1601, 1510, 1451, 1422, 1376, 1353, 1258, 1170, 1023, 980, 846 cm$^{-1}$; $[\alpha]_D^{24}$=−1.6 (c 1.0, EtOH).

《3.1.14. 1-(3-methoxyphenyl)-3-phenyl pentanone 11n》

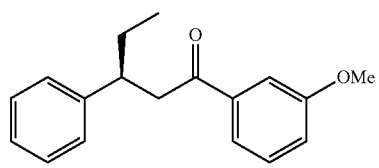

11n $^1$H NMR (400 MHz, CDCl$_3$) δ7.50 (d, J=7.2 Hz, 1H), 7.43 (s, 1H), 7.08-7.35 (m, 6H), 7.07 (d, J=2.4 Hz, 1H), 3.82 (s, 3H), 3.22-3.30 (m, 3H), 1.76-1.79 (m, 1H), 1.63-1.68 (m, 1H), 0.81 (t, J=7.2 Hz, 3H); $^{13}$C NMR (100 MHz, CDCl$_3$) δ199.0 (C), 159.8 (C), 144.7 (C), 138.7 (C), 129.5 (CH), 128.4 (CH), 127.6 (CH), 126.3 (CH), 120.7 (CH), 119.4 (CH), 112.3 (CH), 55.41 (CH$_3$), 45.7 (CH$_2$), 43.1 (CH), 29.2 (CH$_2$), 12.1 (CH$_3$); IR (KBr) v=3062, 3028, 2962, 2931, 2874, 1683, 1597, 1583, 1453, 1429, 1368, 1332, 1258, 1167, 1046, 1026, 995, 876 cm$^{-1}$; $[\alpha]_D^{24}$=+11.5 (c 1.0, EtOH).

《3.1.15. 3-Cyclohexyl-1-phenyl-pentanone 11o》

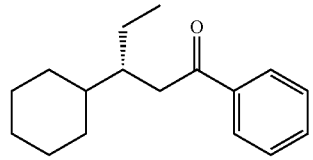

11o $^1$H NMR (400 MHz, CDCl$_3$) δ7.94 (d, J=7.6 Hz, 2H), 7.41-7.54 (m, 3H), 2.96 (dd, J=16.2 and 5.5 Hz, 1H), 2.75 (dd, J=16.2 and 7.2 Hz, 1H), 1.91-1.97 (m, 1H), 1.62-1.76 (m, 5H), 1.00-1.47 (m, 8H), 0.85 (t, J=7.2 Hz, 3H); $^{13}$C NMR (100 MHz, CDCl$_3$) δ201.1 (C), 137.5 (C), 132.7 (CH), 128.5 (CH), 128.1 (CH), 41.0 (CH), 40.2 (CH), 40.2 (CH$_2$), 30.2 (CH$_2$), 29.3 (CH$_2$), 26.8 (CH$_2$), 24.0 (CH$_2$), 12.0 (CH$_3$); IR (KBr) v=3061, 2959, 2924, 2852, 1683, 1598, 1581, 1448, 1373, 1314, 1276, 1205, 1012, 971, 750 cm$^{-1}$; $[\alpha]_D^{24}$=−2.1 (c 0.5, EtOH).

《3.1.16. 3-Methyl-1-phenyl-pentanone 11p》

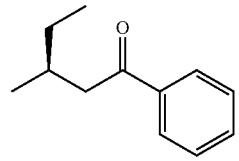

11p $^1$H NMR (400 MHz, CDCl$_3$) δ 7.93 (d, J=7.2 Hz, 2H), 7.50-7.54 (m, 1H), 7.41-7.44 (m, 2H), 2.93 (dd, J=15.6 Hz, 1H), 2.72 (dd, J=15.6 Hz, 1H), 2.02-2.09 (m, 1H), 1.35-1.44 (m, 1H), 1.21-1.31 (m, 1H), 0.90 (t, J=7.6 Hz, 3H); $^{13}$C NMR (100 MHz, CDCl$_3$) δ 200.4 (C), 137.3 (C), 132.8 (CH), 128.5 (CH), 128.0 (CH), 45.5 (CH$_2$), 31.3 (CH), 29.6 (CH$_2$), 19.5 (CH$_3$), 11.4 (CH$_3$); IR (KBr) v=3062, 2961, 2928, 2876, 1683, 1598, 1581, 1449, 1367, 1284, 1207, 1181, 1017, 966, 915 cm$^{-1}$; $[\alpha]_D^{24}$=+8.9 (c 1.0, EtOH).

Although the present invention has been explained in relation to its preferred embodiment, it is to be understood that many other possible modifications and variations can be made without departing from the spirit and scope of the invention as hereinafter claimed.

What is claimed is:

1. A method of enantioselective addition to enones, comprising: reacting $R_3(CH_2)_pCH=CR_5C(=O)Y(CH_2)_qR_4$ with $R_6ZnR_7$ in the presence of a compound represented by the following formula (I) and a transition metal catalyst, (I)

[Structure showing bicyclic compound with OH and N(R1)(R2) substituents]

wherein $R_1$ and $R_2$ taken together is $(CH_2)_m X(CH_2)_n$;

each of $R_3$ and $R_4$, independently, is alkyl, alkenyl, cycloalkyl, cycloalkenyl, heterocycloalkyl, heterocycloalkenyl, aryl, or heteroaryl, or $R_3$ and $R_4$ taken together is alkylene, alkenylene, cycloalkylene, cycloalkenylene, heterocycloalkylene, heterocycloalkenylene, arylene, or heteroarylene;

$R_5$ is hydrogen, halogen, nitro, alkyl, alkenyl, cycloalkyl, cycloalkenyl, heterocycloalkyl, heterocycloalkenyl, aryl, or heteroaryl;

each of $R_6$ and $R_7$, independently, is alkyl, alkenyl, cycloalkyl, cycloalkenyl, heterocycloalkyl, heterocycloalkenyl, aryl;

X is O, S, or $CH_2$;

Y is O, S, or a bond;

each of p and q, independently, is an integer of 0 to 30; and each of m and n, independently, is 1, 2 or 3, and the sum of m and n is 3 or 4.

2. The method as claimed in claim 1, wherein $R_1$ and $R_2$ taken together is $(CH_2)_m X(CH_2)_n$;

each of $R_3$ and $R_4$, independently, is unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_r R_a$; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $(CH_2)_r CH=CH(CH_2)_k R_a$; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or $R_3$ and $R_4$ taken together is unsubstituted or substituted $C_{1-30}$ alkylene by one or more selected from the group consisting of halogen, cyano, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{2-30}$ alkenylene by one or more selected from the group consisting of halogen, cyano, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ arylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroarylene by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

$R_5$ is hydrogen, halogen, nitro, unsubstituted or substituted $C_{1-30}$ alkyl by one or more selected from the group consisting of halogen, cyano, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{2-30}$ alkenyl by one or more selected from the group consisting of halogen, cyano, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituteor substituted 5-14 membered heterocycloalkenyl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

each of $R_6$ and $R_7$ independently is unsubstituted or substituted $C_{1-30}$ alkyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl;

unsubstituted or substituted $C_{2-30}$ alkenyl by one or more of halogen, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and $C_{5-14}$ heteroaryl; unsubstituted or substituted $C_{5-14}$ cycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{5-14}$ cycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted 5-14 membered heterocycloalkenyl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; unsubstituted or substituted $C_{6-14}$ aryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or unsubstituted or substituted 5-14 membered heteroaryl by one or more of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

$R_a$ is substituted $C_{6-14}$ aryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or substituted 5-14 membered heteroaryl by one or more selected from the group consisting of halogen, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

i is an integer of 1 to 30; and each of r and k independently is an integer of 0 to 30.

3. The method as claimed in claim 1, wherein $R_1$ and $R_2$ taken together is $(CH_2)_mX(CH_2)_n$;

each of $R_3$ and $R_4$, independently, is unsubstituted or substituted $C_{1-10}$ alkyl by one or more selected from the group consisting of $C_{6-14}$ aryl and 5-14 membered heteroaryl; $(CH_2)_iR_a$; unsubstituted or substituted $C_{2-10}$ alkenyl by one or more selected from the group consisting of $C_{6-14}$ aryl and 5-14 membered heteroaryl; $(CH_2)_rCH=CH(CH_2)_kR_a$; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or $R_3$ and $R_4$ taken together is unsubstituted or substituted $C_{1-10}$ alkylene by one or more selected from the group consisting of halogen, cyano, $C_{1-10}$ alkoxy, $C_{1-10}$ haloalkyl, $CO_2$—$C_{1-10}$ alkyl and $CO_2$—$C_{2-10}$ alkenyl; unsubstituted or substituted $C_{2-10}$ alkenylene by one or more selected from the group consisting of halogen, cyano, $C_{1-10}$ alkoxy, $C_{1-10}$ haloalkyl, $CO_2$—$C_{1-10}$ alkyl and $CO_2$—$C_{2-10}$ alkenyl; unsubstituted or substituted $C_{5-14}$ cycloalkylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted $C_{5-14}$ cycloalkenylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heterocycloalkylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heterocycloalkenylene by one or more selected from the group consisting of halogen, cyano, $C_{1-30}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted $C_{6-14}$ arylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or unsubstituted or substituted 5-14 membered heteroarylene by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl;

$R_5$ is hydrogen, halogen, nitro, unsubstituted $C_{1-10}$ alkyl, or unsubstituted $C_{2-10}$ alkenyl;

$R_6$ is unsubstituted $C_{1-10}$ alkyl;

$R_7$ is unsubstituted or substituted $C_{1-10}$ alkyl by one or more selected from the group consisting of $C_{6-14}$ aryl and 5-14 membered heteroaryl; unsubstituted or substituted $C_{2-10}$ alkenyl by one or more selected from the group consisting of $C_{6-14}$ aryl and 5-14 membered heteroaryl; unsubstituted $C_{5-14}$ cycloalkyl; unsubstituted $C_{5-14}$ cycloalkenyl; unsubstituted or substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; unsubstituted or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-20}$ alkenyl;

$R_a$ is substituted $C_{6-14}$ aryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl; or substituted 5-14 membered heteroaryl by one or more selected from the group consisting of halogen, cyano, $C_{1-10}$ alkyl, $C_{2-10}$ alkenyl, $C_{1-10}$ alkoxy, $C_{1-10}$ haloalkyl, $CO_2$—$C_{1-10}$ alkyl and $CO_2$—$C_{2-10}$ alkenyl;

i is an integer of 1 to 10; and each of r and k independently is an integer of 0 to 10.

4. The method as claimed in claim 3, wherein each of p and q independently is an integer of 0 to 10.

5. The method as claimed in claim 1, wherein the transition metal catalyst is a nickel complex.

6. The method as claimed in claim 5, wherein the mole ratio of the compound represented by the formula (I) to the transition metal catalyst ranges from 1:1 to 100:1.

7. The method as claimed in claim 6, wherein the mole ratio of the compound represented by the formula (I) to the transition metal catalyst ranges from 13:1 to 25:1.

8. The method as claimed in claim 6, wherein the compound represented by the formula (I) is used in an amount of 5 to 20 mol % based on $R_3(CH_2)_pCH=CR_5C(=O)Y(CH_2)_qR_4$.

9. The method as claimed in claim 6, wherein the transition metal catalyst is used in an amount of 0.1 to 10 mol % based on $R_3(CH_2)_pCH=CR_5C(=O)Y(CH_2)_qR_4$.

10. The method as claimed in claim 1, wherein $R_6ZnR_7$ is used in an amount of 1 to 5 equivalents based on $R_3(CH_2)_pCH=CR_5C(=O)Y(CH_2)_qR_4$.

11. The method as claimed in claim 1, wherein $R_3(CH_2)_p CH=CR_5C(=O)Y(CH_2)_qR_4$ is reacted with $R_6ZnR_7$ at a temperature in a range from 0° C. to −60° C.

12. The method as claimed in claim 11, wherein $R_3(CH_2)_p CH=CR_5C(=O)Y(CH_2)_qR_4$ is reacted with $R_6ZnR_7$ at a temperature in a range from −20° C. to −60° C.

13. The method as claimed in claim 1, wherein $R_3(CH_2)_p CH=CR_5C(=O)Y(CH_2)_qR_4$ is reacted with $R_6ZnR_7$ in an aprotic solvent.

14. The method as claimed in claim 13, wherein the concentration of $R_3(CH_2)_p CH=CR_5C(=O)Y(CH_2)_qR_4$ in the aprotic solvent ranges from 0.05 M to 2 M.

15. The method as claimed in claim 14, wherein the concentration of $R_3(CH_2)_p CH=CR_5C(=O)Y(CH_2)_qR_4$ in the aprotic solvent ranges from 0.2 M to 1 M.

16. The method as claimed in claim 13, wherein the aprotic solvent is selected from the group consisting of acetonitrile, propionitrile, butyronitrile, isobutyronitrile, tetrahydrofuran, ether, toluene, dichloromethane, n-haxane and a mixture thereof.

17. The method as claimed in claim 1, wherein the sum of m and n is 4 when X is O or S.

18. The method as claimed in claim 1, wherein m is 1 or 2, and n is 2.

19. The method as claimed in claim 1, wherein $R_1$ and $R_2$ taken together is $(CH_2)_4$, $(CH_2)_5$ or $(CH_2)_2O(CH_2)_2$.

* * * * *